(12) United States Patent
Balashov et al.

(10) Patent No.: US 9,970,060 B2
(45) Date of Patent: May 15, 2018

(54) QUANTITATION AND PROFILING OF VAGINAL MICROFLORA

(71) Applicant: Medical Diagnostic Laboratories, LLC, Hamilton, NJ (US)

(72) Inventors: Sergey Balashov, Hamilton, NJ (US); Martin E. Adelson, East Windsor, NJ (US); Charronne Davis, Mahwah, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 0 days. days.

(21) Appl. No.: 13/682,071

(22) Filed: Nov. 20, 2012

(65) Prior Publication Data

US 2013/0316922 A1   Nov. 28, 2013

Related U.S. Application Data

(60) Provisional application No. 61/629,656, filed on Nov. 23, 2011, provisional application No. 61/668,106, filed on Jul. 5, 2012.

(51) Int. Cl.
*C12Q 1/68* (2018.01)

(52) U.S. Cl.
CPC ......... *C12Q 1/689* (2013.01); *C12Q 2600/16* (2013.01)

(58) Field of Classification Search
USPC .............................. 435/6.12, 91.2; 536/24.33
See application file for complete search history.

(56) References Cited

U.S. PATENT DOCUMENTS

| | | | |
|---|---|---|---|
| 6,194,454 B1* | 2/2001 | Dow ............................. | 514/522 |
| 6,596,239 B2* | 7/2003 | Williams ............ | B01J 19/0046 347/46 |
| 6,863,362 B2* | 3/2005 | Reichel ................. | B01L 3/0268 347/19 |
| 2006/0041954 A1* | 2/2006 | Lu et al. ....................... | 800/279 |
| 2007/0178495 A1* | 8/2007 | Fredricks et al. ................ | 435/6 |
| 2010/0075306 A1* | 3/2010 | Bretelle ............... | C12Q 1/6851 435/6.15 |
| 2010/0249995 A1* | 9/2010 | Williams ........... | G06Q 30/0601 700/233 |
| 2011/0151462 A1* | 6/2011 | Tynan et al. ................. | 435/6.12 |
| 2011/0212852 A1* | 9/2011 | Getman ................. | C12Q 1/689 506/9 |
| 2012/0264126 A1* | 10/2012 | Johnson ................. | C12Q 1/689 435/6.11 |

FOREIGN PATENT DOCUMENTS

WO   WO2011068679   *   6/2011   ............... C12Q 1/68

OTHER PUBLICATIONS

De Backer et al., BMC Microbiology, 2007, (7) pp. 1-13.*
Swango et all, Forensic Science International, 2007, 170, pp. 35-45.*
Lowe et al., Nucleic Acids Research, 1990, vol. 18, No. 7, pp. 1757-1761.*
Menard et al., Clinical Infectious Diseases, 2008, 47, pp. 33-43.*
Marrazzo, Jeanne, Anaerobe, 17, available online Apr. 2011, pp. 186-190.*
Linhares et al., Review Assoc Med. Bras., 2010, 56(3), pp. 370-374.*
"Bacterial Vaginosis (with Lactobacillus Profiling) qPCR Panel", Medical Diagnostic Laboratories, L.L.C., released Jul. 2011.*
Zhou et al., International Society for Microbial Ecology, 2007, 1, pp. 121-133.*
Nuleic acid sequences search reports AC: AGI42825, AGI42789, AGI42854.*
De Backer E, Verhelst R, Verstraelen H, Alqumber MA, Burton JP, Tagg JR, Temmerman M, Vaneechoutte M. Quantitative determination by real-time PCR of four vaginal Lactobacillus species, Gardnerella vaginalis and Atopobium vaginae indicates an inverse relationship between L. gasseri and L. iners. BMC Microbiol. Dec. 19, 2007; 7:115.*
Allsworth, J., Peipert., J. F. Prevalence of bacterial vaginosis: 2001-2004 National Health and Nutrition Examination Survey data, Jan. 2007 Obstet Gynecol, 109:114-120.
Donati L., et al., Vaginal microbial flora and outcome of pregnancy. Dec. 5, 2009, Arch Gynecol Obstet. 281 (4):589-600.
Forsum, U., Hallen, A., Larsson, P. G., Bacterial vaginosis—a laboratory and clinical diagnostics enigma. Dec. 17, 2004, APMIS. 113(3):153-61.
Fredricks, D. N., Fiedler, T. L., Thomas, K. K., Oakley, B. B., Marrazzo. J. M. Targeted PCR for detection of vaginal bacteria associated with bacterial vaginosis. Aug. 8, 2007, J Clin Microbiol 45:3270-3276.
Fredricks, D. N., Fiedler, T. L., Thomas, K. K., Mitchell, C. M., Marrazzo. J. M., Changes in vaginal bacterial concentrations with intravaginal metronidazole therapy for bacterial vaginosis as assessed by quantitative PCR. Jan. 14, 2009, J Clin Microbiol 47:721-726.
Jakobsson, T., Forsum, U. Lactobacillus iners: a marker of changes in the vaginal flora, Jul. 25, 2007, J Clin Microbiol. 45(9):3145.
Lamont, R. F, Sobel, J. D., Akins, R. A., Hassan, S. S., Chaiworapongsa, T., Kusanovic, J. P., Romero, R., The vaginal microbiome: new information about genital tract flora using molecular based techniques. Jan. 20, 2011, BJOG. 118(5):533-49.
Menard, J. P, Mazouni, C., Fenollar, F., Raoult, D., Boubli, L., Bretelle F., Diagnostic accuracy of quantitative real-time PCR assay versus clinical and Gram stain identification of bacterial vaginosis, Sep. 3, 2010, Eur J Clin Microbiol Infect Dis. 29(12):1547-52.
Nugent, R. P., Krohn, M. A, Hillier, S. L., Reliability of diagnosing bacterial vaginosis is improved by a standardized method of gram stain interpretation. Feb. 1991, J Clin Microbiol. 29(2):297-301.
Ravel,J, Gajer P, Abdo Z, Schneider GM, Koenig SS, McCulle SL, Karlebach S, Gorle R, Russell J, Tacket CO, Brotman RM, Davis CC, Ault K, Peralta L, Forney LJ. Vaginal microbiome of reproductive-age women. Mar. 15, 2011. Proc Natl Acad Sci U S A., 108, Suppl 1:4680-7.

(Continued)

Primary Examiner — Samuel C Woolwine
Assistant Examiner — Olayinka A Oyeyemi
(74) Attorney, Agent, or Firm — Terence J. Bogie; Jessica Downing

(57) ABSTRACT

Disclosed are methods of quantifying microflora in vaginal samples. Quantitative assessment of vaginal microflora by real-time PCR to create a profiling of *Lactobacillus* species, *Gardnerella vaginalis*, *Atopobium vaginae*, *Megasphaera* Type 1 and Type 2 and BVAB2 permits evaluation of bacterial vaginosis. Kits containing reagents for quantitative assessment of microflora are also disclosed.

3 Claims, 12 Drawing Sheets

(56) References Cited

OTHER PUBLICATIONS

Schwebke, J. R, Hillier, S. L, Sobel, J. D., McGregor, J. A., Sweet, R. L., Validity of the vaginal gram stain for the diagnosis of bacterial vaginosis. Oct. 1996, Obstet Gynecol. 88(4 Pt 1):573-6.

Sha, B. E., Chen, H. Y., Wang, Q. J., Zariffard, M. R., Cohen, M. H., Spear, G. T., Utility of Amsel criteria, Nugent score, and quantitative PCR for Gardnerella vaginalis, Mycoplasma hominis, and *Lactobacillus* spp. for diagnosis of bacterial vaginosis in human immunodeficiency virus-infected women. Sep. 2005, J Clin Microbiol. 43 (9):4607-12.

Srinivasan, S., Liu C., Mitchell, C. M., Fiedler, T. L., Thomas, K. K., Agnew, K. J., Marrazzo, J. M., Fredricks, D. N. Temporal variability of human vaginal bacteria and relationship with bacterial vaginosis. Apr. 15, 2010, PLoS One. 15;5(4):e10197.

Zozaya-Hinchliffe, M., Lillis, R., Martin, D.H., Ferris, M. J., Quantitative PCR assessments of bacterial species in women with and without bacterial vaginosis. Mar. 19, 2010, J Clin Microbiol. 48(5):1812-9.

Forsum, U., Hoist, E., Larsson, P. G., Vasquez, A., Jakobsson, T., Mattsby-Baltzer I. Bacterial vaginosis—a microbiological and immunological enigma. Dec. 10, 2005, APMIS. 113(2):81-90.

\* cited by examiner

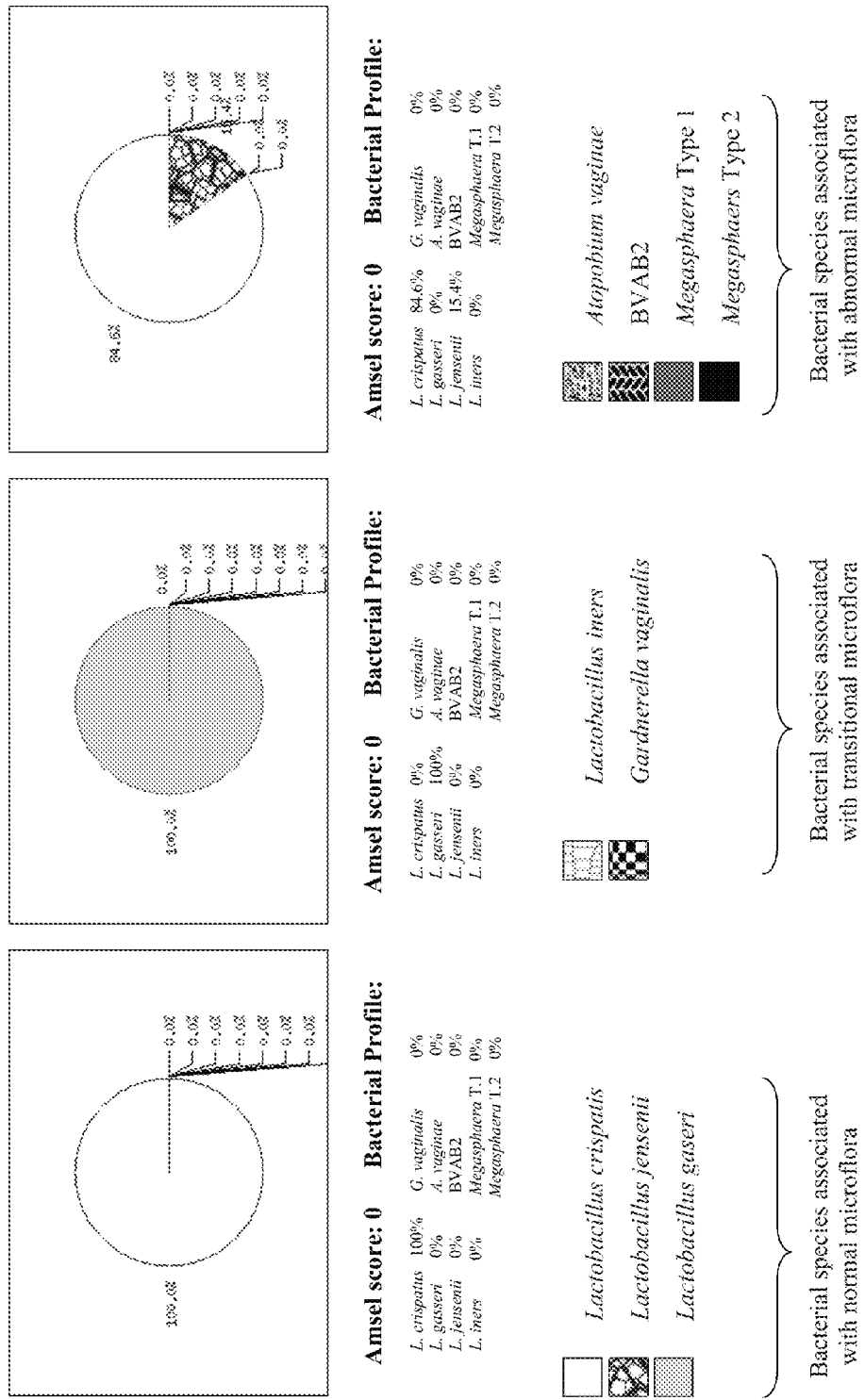
Figure 1a  Normal Vaginal Microflora

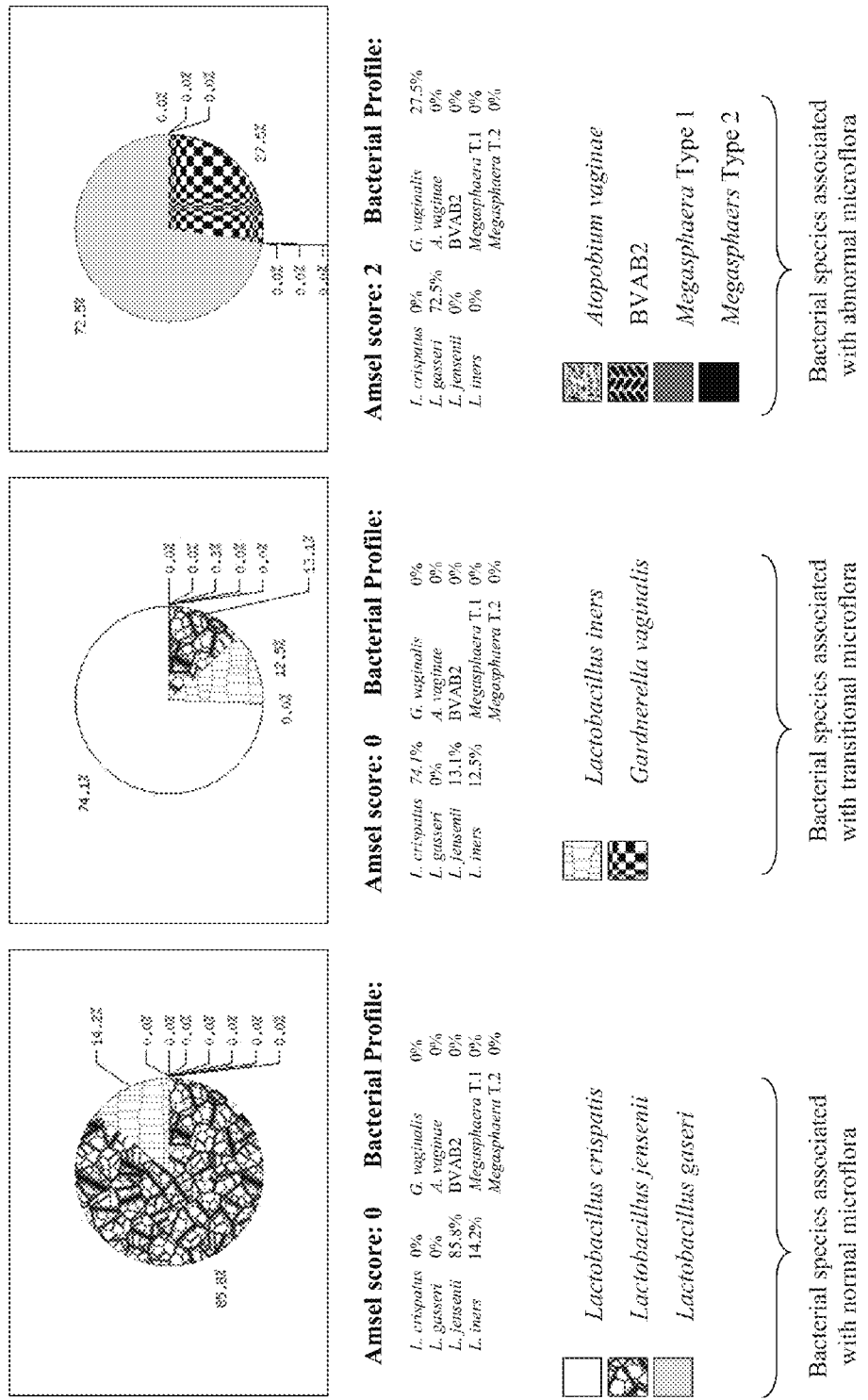
Figure 1b  Normal Vaginal Microflora

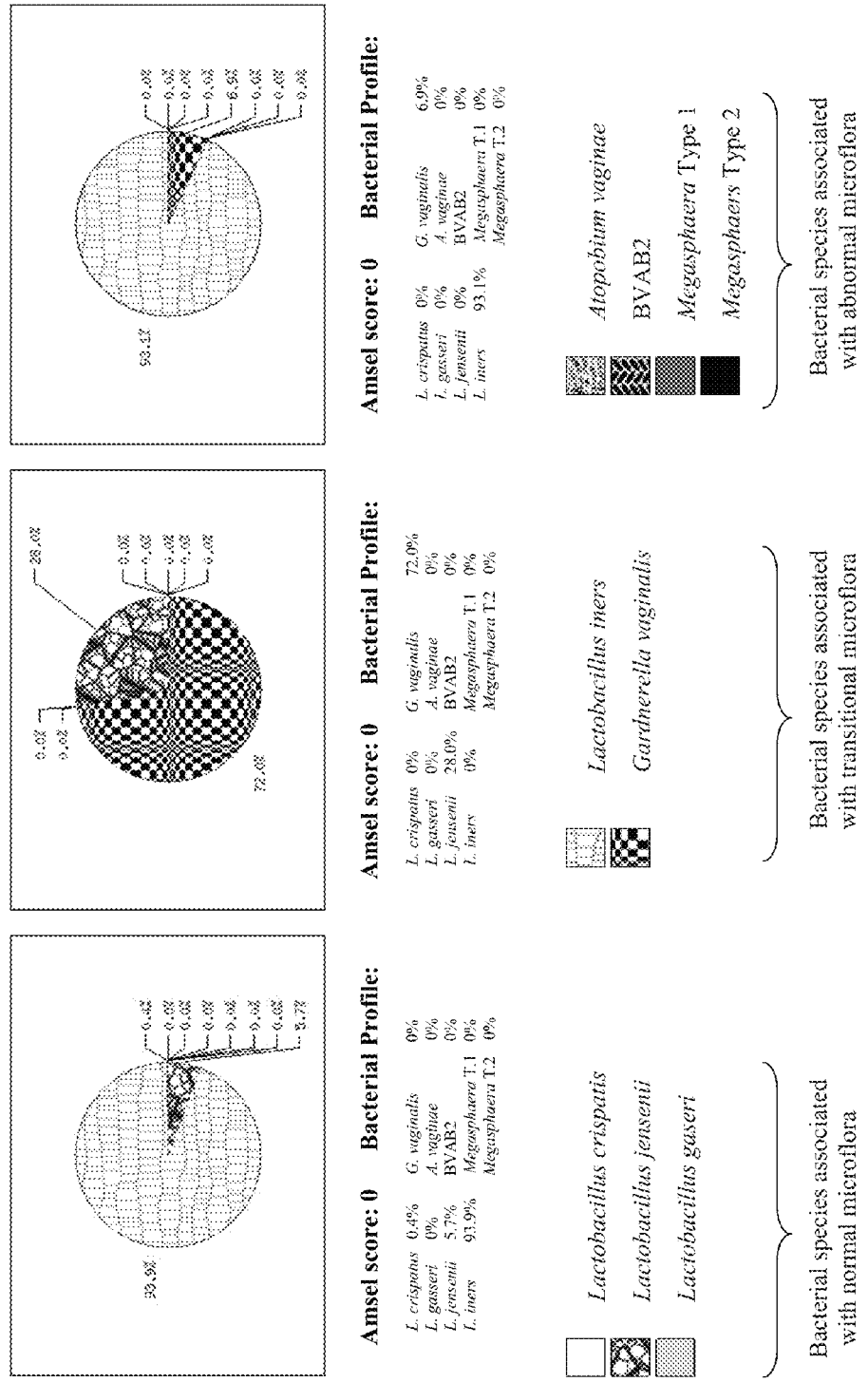
Figure 2a   Intermediate Vaginal Microflora

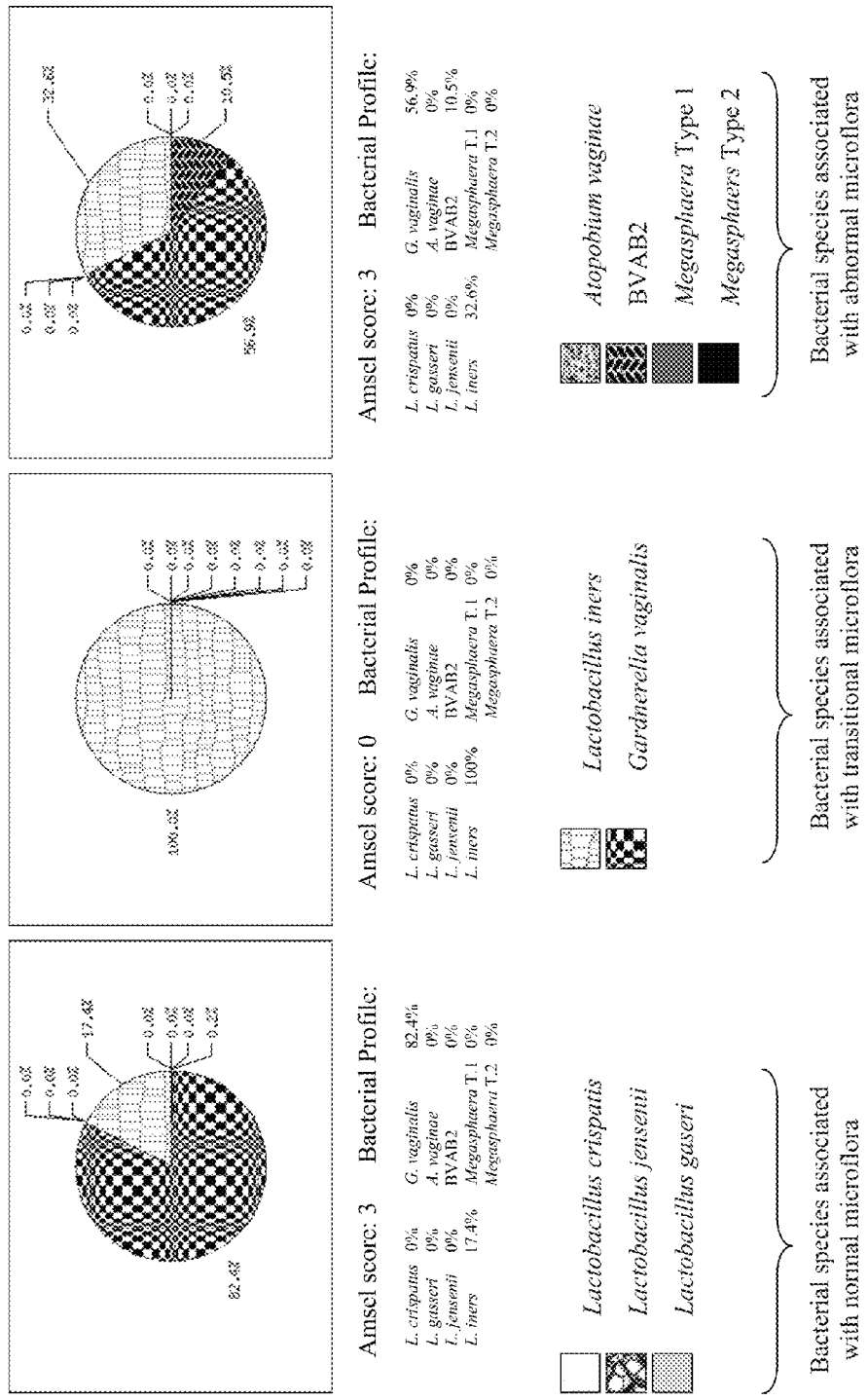
Figure 2b   Intermediate Vaginal Microflora

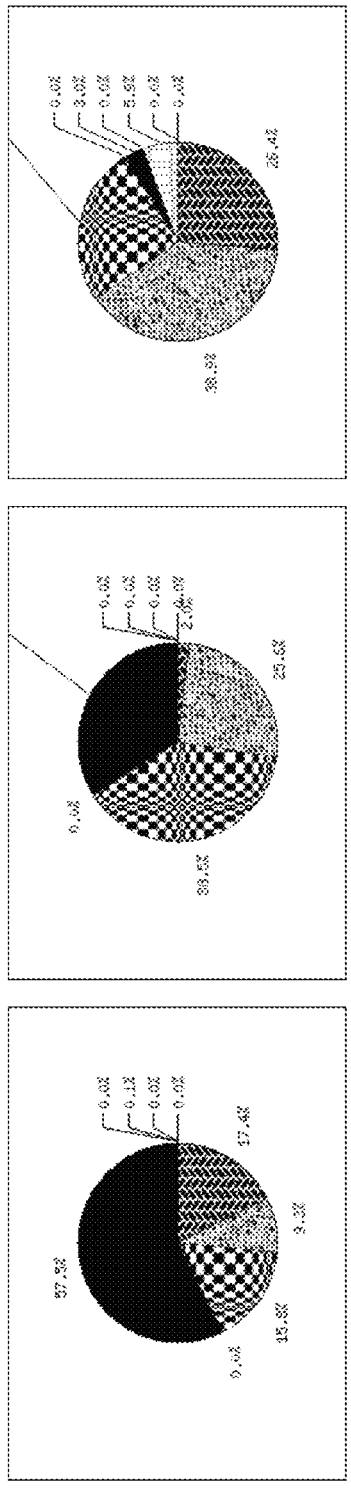
Figure 3a   Abnormal Vaginal Microflora

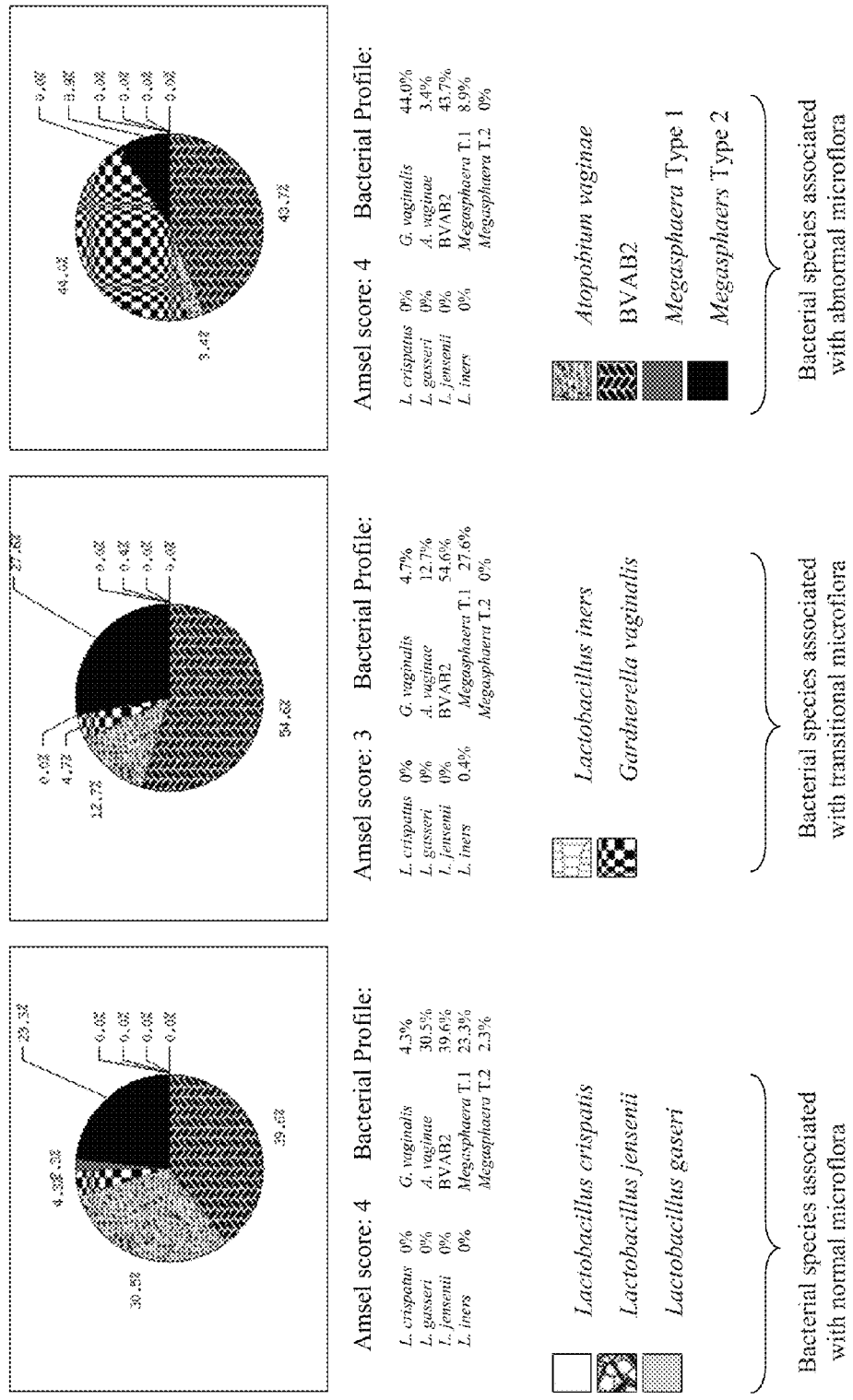
Figure 3b  Abnormal Vaginal Microflora

QUANTITATION AND PROFILING OF VAGINAL MICROFLORA

CROSS-REFERENCE TO RELATED APPLICATIONS

This application claims the benefit under 35 U.S.C. § 119(e) to U.S. Provisional Application Nos. 61/629,656 and 61/668,106, filed Nov. 23, 2011 and Jul. 5, 2012, respectively, the content of which is incorporated by reference herein in its entirety.

FIELD OF THE INVENTION

The present invention generally relates to the field of diagnostic assays for detecting and quantifying as well as profiling the vaginal microflora for personalized diagnosis in normal women and women with bacterial vaginosis. Specifically, the present invention provides a relative quantitative assessment of vaginal microflora by real-time PCR in order to create a profile useful in the diagnosis for bacterial vaginosis of a woman, based on the vaginal microflora that includes *Lactobacillus crispatus, Lactobacillus gasseria, Lactobacillus jensenii, Lactobacillus iners, Gardnerella vaginalis, Atopobium vaginae, Megasphaera* Type 1, *Megasphaera* Type 2 and BVAB2. The relative quantitation of the selected individual microflora species is useful in assessing the health status (normal, transitional or bacterial vaginosis) of the vaginal microflora in a woman.

BACKGROUND OF THE INVENTION

Vaginal bacterial flora is an important part of human-associated microbiome. The environment of the human vagina differs from that of other human body's compartments. Human vagina is populated by multiple distinct microorganisms adapted to the particular environment. It is believed that vaginal microflora is a dynamic microbial system prone to changes in its species composition due to various exogenous and endogenous influences. There is no single vaginal "core microbiome", but rather a "space" of distinctly different microbial communities. Relative dynamics of vaginal communities is still largely unknown, due to the lack of extensive longitudinal studies. Profound change in the microbial composition may take place during menstrual cycles or antibiotic therapy.

Specific vaginal communities are tightly linked to bacterial vaginosis (BV). Microbial species populating these communities are designated as BV-associated bacteria (BVAB). Most of the BVAB are fastidious anaerobic bacteria which are difficult to culture or yet to be cultured. On the contrary, vaginal communities dominated by lactobacilli are frequently associated with the absence of BV clinical symptoms. Taxonomical complexities of these vaginal communities are difficult to ascertain because they are usually dominated by a single *Lactobacillus* species.

Scarce information exists as to whether there is a strong association of taxonomic groups of specific vaginal microflora that may define as valid markers for different vaginal microbial conditions. Little is known regarding the relative amounts of these specific bacteria in vaginal samples, thus rendering it difficult for the predictive assessment of vaginal microflora status. To the best of the present inventors' knowledge, there has been no correlation made between bacterial qPCR quantitative results and the clinical diagnosis of BV according to the Amsel criteria.

There is a continuing need in assessing the profile of vaginal microflora and how they correlate with the progression of bacterial vaginosis. The present invention cures the above-mentioned defects and provides a useful quantitative detection assay for a selected group of nine (9) bacterial species. Disclosed herein are the inventive embodiments describing a dynamic nature of vaginal microflora. The present assay utilizes real-time PCR assays to quantity four (4) *Lactobacillus* species, as well as *Gardnerella vaginalis, Atopobium vaginae, Megasphaera* Type 1, *Megasphaera* Type 2 and BVAB2.

SUMMARY OF THE INVENTION

The present invention provides a correlation between relative quantitation of specific vaginal microflora with bacterial vaginosis. The present invention further provides real-time PCR assays for quantifying *Lactobacillus* species, *Gardnerella vaginalis, Atopobium vaginae, Megasphaera* Type 1 and Type 2 and BVAB2. The application of the correlation is useful in the diagnosis of bacterial vaginosis.

In one aspect, the present invention provides a real-time PCR assay for quantifying *Lactobacillus* species, *Gardnerella vaginalis, Atopobium vaginae, Megasphaera* Type 1 and Type 2 and BVAB2, wherein the *Lactobacillus* species include *Lactobacillus crispatus, Lactobacillus gasseria, Lactobacillus jensenii* and *Lactobacillus iners*, and wherein an increase in relative expression of at least one of the *Lactobacillus crispatus, Lactobacillus gasseria, Lactobacillus jensenii* in a biological sample (e.g., obtained from vaginal source) is an indicative of a normal vaginal microflora.

In one aspect, the present invention provides a real-time PCR assay for quantifying *Lactobacillus* species, *Gardnerella vaginalis, Atopobium vaginae, Megasphaera* Type 1 and Type 2 and BVAB2, wherein *Lactobacillus* species include *Lactobacillus crispatus, Lactobacillus gasseria, Lactobacillus jensenii* and *Lactobacillus iners*, and wherein an increase in relative expression of *Lactobacillus iners* and *Gardnerella vaginalis* in a biological sample (e.g., obtained from vaginal source) is an indicative of a transitional vaginal microflora.

In one aspect, the present invention provides a real-time PCR assay for quantifying *Lactobacillus* species, *Gardnerella vaginalis, Atopobium vaginae, Megasphaera* Type 1 and Type 2 and BVAB2, wherein *Lactobacillus* species include *Lactobacillus crispatus, Lactobacillus gasseria, Lactobacillus jensenii* and *Lactobacillus iners*, and wherein an increase in relative expression of *Atopobium vaginae, Megasphaera* Type 1 and Type 2 and BVAB2 in a biological sample (obtained from vaginal source) is an indicative of an abnormal vaginal microflora. An exemplary abnormal vaginal microflora includes that of bacterial vaginosis.

In one aspect, the present invention provides a quantitative assay to quantify, in a real-time PCR, the relative amount of *Lactobacillus* species, *Gardnerella vaginalis, Atopobium vaginae, Megasphaera* Type 1 and Type 2 and BVAB2, wherein *Lactobacillus* spp. include *Lactobacillus crispatus, Lactobacillus gasseria, Lactobacillus jensenii* and *Lactobacillus iners*.

In one aspect, the present invention provides primers and probes used in the three (3) quantitative-PCRs. The present invention also provides uniplex PCRs to respectively quantify *Gardnerella vaginalis, Atopobium vaginae*, and BVAB2. The forward/reverse primers and fluorescently-labeled probes for each of the uniplex PCRs are species-specific and do not cross-react with other species.

In one aspect, the present invention provides a multiplex PCR to quantify four (4) *Lactobacillus* species. A single pair of primers (i.e., a forward primer and a reverse primer) coupled with species-specific probes are provided to target *Lactobacillus crispatus, Lactobacillus gasseri, Lactobacillus jensenii*, and *Lactobacillus iners*.

In one aspect, the present invention provides a multiplex PCR to quantify *Megasphaera* spp. A single primer pair (i.e., a forward primer and a reverse primer), when coupled with species-specific probes, specifically detects *Megasphaera* Type 1 and *Megasphaera* Type 2.

In one aspect, the present invention provides a method of profiling based on an individual (i.e., a woman) the relative amounts of *Lactobacillus crispatus, Lactobacillus gasseri, Lactobacillus jensenii, Lactobacillus iners, Gardnerella vaginalis, Atopobium vaginae, Megasphaera* Type 1 and *Megasphaera* Type 2, and BVAB2.

In another aspect, the present invention provides a method of diagnosing bacterial vaginosis, comprising the steps of: (i) obtaining a biological sample (vaginal sample) from a woman suspected of having a bacterial vaginosis; (ii) quantifying the micro-organisms of *Lactobacillus* species (including *Lactobacillus crispatus, Lactobacillus gasseria, Lactobacillus jensenii* and *Lactobacillus iners*), *Gardnerella vaginalis, Atopobium vaginae, Megasphaera* Type 1 and Type 2 and BVAB2; and (iii) profiling the relative amounts of *Lactobacillus crispatus, Lactobacillus gasseria, Lactobacillus jensenii, Lactobacillus iners, Gardnerella vaginalis, Atopobium vaginae, Megasphaera* Type 1 and Type 2 and BVAB2 present in said biological sample.

In another aspect, the present invention provides a method of diagnosing transitional vaginal microflora in a woman, comprising the steps of: (i) obtaining a biological sample (vaginal sample) from a woman; (ii) quantifying the micro-organisms of *Lactobacillus* species (including *Lactobacillus crispatus, Lactobacillus gasseria, Lactobacillus jensenii* and *Lactobacillus iners*), *Gardnerella vaginalis, Atopobium vaginae, Megasphaera* Type 1 and Type 2 and BVAB2; and (iii) profiling the relative amounts of *Lactobacillus crispatus, Lactobacillus gasseria, Lactobacillus jensenii, Lactobacillus iners, Gardnerella vaginalis, Atopobium vaginae, Megasphaera* Type 1 and Type 2 and BVAB2 present in said biological sample.

In yet another aspect, the present invention provides an article of manufacture comprising a packaging material; and detection agents for quantifying *Lactobacillus crispatus, Lactobacillus gasseria, Lactobacillus jensenii* and *Lactobacillus iners, Gardnerella vaginalis, Atopobium vaginae, Megasphaera* Type 1 and Type 2 and BVAB2. The article of manufacture may further comprise an instruction for detecting and quantifying the microflora present in vaginal samples, as well as profiling the vaginal microflora.

BRIEF DESCRIPTION OF THE DRAWINGS

FIG. 1a and FIG. 1b depict a total of six (6) exemplary profiling (i.e., reflecting the relative amounts of the nine (9) examined bacterial species) in vaginal samples from normal subjects (diagnosed with Amsel scores 0-2). The profiling is characterized by normal vaginal microflora. The relative amounts of the bacterial species were determined by qPCRs.

FIG. 2a and FIG. 2b depict a total of six (6) exemplary profiling of the nine (9) examined bacterial species in vaginal samples from women (diagnosed with Amsel scores 0-2). The profiling is characterized by transitional vaginal microflora. The relative amounts of the bacterial species were determined by qPCRs.

FIG. 3a and FIG. 3b depict a total of six (6) exemplary profiling of the nine (9) examined bacterial species in vaginal samples from women (diagnosed with bacterial vaginosis with Amsel scores 3-4). The relative amounts of the bacterial species were determined by qPCRs.

DETAILED DESCRIPTION OF THE INVENTION

Figure 4A:
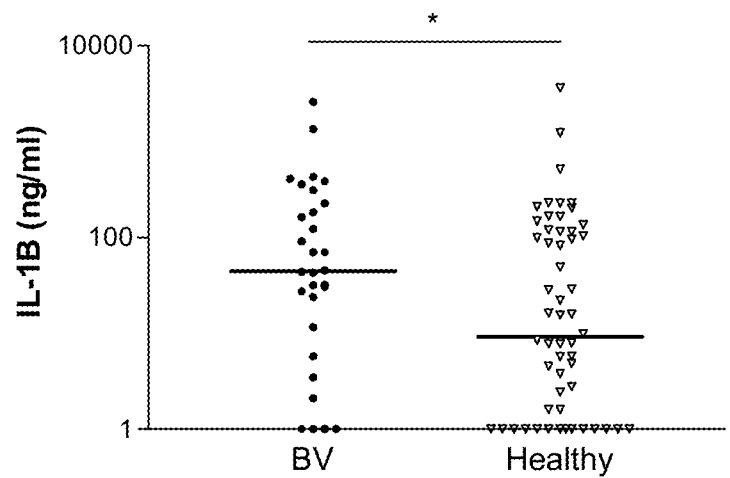
FIG. 4a, FIG. 4b, FIG. 4c and FIG. 4d depict vaginal levels of (a) interleukin-1 beta (IL-1$\beta$), (b) interleukin-8 (IL-8), (c) human beta-defensin 2 (hBD-2) and (d) lactoferrin (LF), among healthy and BV patients. Horizontal bar indicates median value for each column. * $P<0.05$, Mann-Whitney U Test.

The present invention can be better understood from the following description of preferred embodiments, taken in conjunction with the accompanying drawings. It should be apparent to those skilled in the art that the described embodiments of the present invention provided herein are merely exemplary and illustrative and not limiting.

Definitions

Various terms used throughout this specification shall have the definitions set out herein.

As used herein, the term "PCR" refers to a polymerase chain reaction. PCR means the amplification of a specific DNA sequence using short oligonucleotides (primers) specific for the terminal of the template sequence. The template-primers mixture is subjected to repeated cycles of heating to separate (melt) the double-stranded DNA and cooling in the presence of nucleotides in the presence of DNA polymerase such that the template sequence is copied at each cycle.

As used herein, the term "uniplex PCR" refers to uniplex polymerase chain reaction. Uniplex PCR is a method for the detection of a single template sequence in an amplified product from a reaction determined by the addition of one pair of oligonucleotide primers.

As used herein, the term "multiplex PCR" refers to the multiplex polymerase chain reaction, and is a detection of more than one template sequence in a mixture by addition of more than one set of oligonucleotide primers.

As used herein, the term "quantitative PCR" (aka "qPCR") refers to the quantitative polymerase chain reaction. Quantitative PCR is a means for quantifying the amount of template DNA present in the original mixture, usually achieved by the addition of a known amount of a target sequence that is amplified by the same primer set but can be differentiated at the end of the reaction.

As used herein, the term "real-time PCR" refers to the real-time polymerase chain reaction. Real-time PCR is a method for the detection and quantitation of an amplified PCR product based on a fluorescent reporter dye; the fluorescent signal increases in direct proportion to the amount of PCR product produced and is monitored at each cycle, 'in real time', such that the time point at which the first significant increase in the amount of PCR product correlates with the initial amount of target template.

As used herein, the term "bacterial vaginosis" (BV) refers to a type of polymicrobial clinical syndrome resulting from replacement of the normal hydrogen peroxide producing *Lactobacillus* species in the vagina with high concentrations of anaerobic bacteria (e.g., *Prevotella* sp. and *Mobiluncus* sp.), *Gardnerella vaginalis, Ureaplasma, Mycoplasma*, and numerous fastidious or uncultivated anaerobes. Some women experience transient vaginal microbial changes, whereas others experience them for a longer interval of time. Among women presenting for care, BV is the most prevalent cause of vaginal discharge or malodor; however, in a nationally representative survey, most women with BV were asymptomatic. The cause of the microbial alteration that characterizes BV is not fully understood, nor is whether BV results from acquisition of a sexually transmitted pathogen. Nonetheless, women with BV are at increased risk for the acquisition of some STDs (e.g., HIV, *N. gonorrhoeae, C. trachomatis*, and HSV-2), complications after gynecologic surgery, complications of pregnancy, and recurrence of BV.

As used herein, the term "diagnosis of bacterial vaginosis" refers to a way of determining the presence or absence of a bacterial vaginosis condition. BV can be diagnosed by the use of clinical criteria (i.e., Amsel diagnostic criteria) or Gram stain (i.e., Nugent score). Other tests, including a DNA probe-based test for high concentrations of *G. vaginalis* (Affirm VP III, Becton Dickinson, Sparks, Md.), a prolineaminopeptidase test card (Pip Activity TestCard, Quidel, San Diego, Calif.), and the OSOM BVBlue test have acceptable performance characteristics compared with Gram stain. Although a card test is available for the detection of elevated pH and trimethylamine, it has low sensitivity and specificity and therefore is not recommended. PCR also has been used in research settings for the detection of a variety of organisms associated with BV, but evaluation of its clinical utility is uncertain. Detection of one organism or group of organisms might be predictive of BV by Gram stain. However, additional evaluations are needed to confirm these associations. Culture of *Gardnerella vaginalis* is not recommended as a diagnostic tool because it is not specific. Cervical Pap tests have no clinical utility for the diagnosis of BV because of their low sensitivity.

As used herein, the term "Amsel criteria" refers to a one of most common clinical approaches for BV diagnostics described by Amsel et al. Positive clinical BV diagnosis is based on the fulfillment of at least three (3) out of the following four (4) criteria: (1) homogeneous, thin, white discharge that smoothly coats the vaginal walls; (2) presence of clue cells on microscopic examination; (3) pH of vaginal fluid >4.5; or (4) a fishy odor of vaginal discharge before or after addition of 10% KOH (i.e., the whiff test) See, Amsel, R., Totten, P. A., Spiegel, C. A., Chen, K. C, Eschenbach, D., Holmes, K. K. 1983. Nonspecific vaginitis. Diagnostic criteria and microbial and epidemiologic associations. *Am. J. Med.* 74(1):14-22.

As used herein, the term "Nugent score" refers to a one of most common laboratory approaches for BV diagnostics described by Nugent et al. The Nugent score is calculated by manual microscopic evaluation of vaginal specimens and assessing relative concentration of Lactobacilli (i.e., long Gram-positive rods), Gram-negative and Gram-variable rods and cocci (i.e., *Gardnerella vaginalis, Prevotella, Porphyromonas*, and *peptostreptococci*), and curved Gram-negative rods (i.e., *Mobiluncus*). Nugent score can range from 0 to 10. A score of 0 to 4 is not consistent with BV. A score of 7 to 10 is consistent with BV. (See, Nugent, R. P., Krohn, M. A, Hillier, S. L., 1991. Reliability of diagnosing bacterial vaginosis is improved by a standardized method of gram stain interpretation. *J. Clin. Microbiol.* 29(2):297-301).

As used herein, the term "microflora" refers to microorganisms of a particular habitat or host organism.

As used herein, the term "normal vaginal microflora" refers to a microflora state that is not associated with any vaginal condition or disease. Normal vaginal microflora is usually dominated by lactobacilli and usually scored from 0 to 4 according to Nugent methodology. The association of lactobacilli with normal microflora has been shown in multiple studies by both conventional microbiological and molecular techniques. Four *Lactobacillus* species: *Lactobacillus jensenii, Lactobacillus gasseri, Lactobacillus iners* and *Lactobacillus crispatus* are considered to be major or dominant vaginal lactobacilli. They are frequently accompanied by less abundant minor *Lactobacillus* species including *Lactobacillus acidophilus, Lactobacillus johnsoni, Lactobacillus vaginalis, Lactobacillus fermentum, Lactobacillus reuteri*, etc. The numerical prevalence of lactobacilli in the vagina prevents its colonization by other pathogens. Many important aspects of women's sexual and reproductive health rely on the protective role of lactobacilli in the vaginal environment.

As used herein, the term "transitional vaginal microflora" (also known as "intermediate vaginal microflora) refers to microflora that presumably represents a transitional stage between normal and abnormal states. Differently from normal and abnormal microflora, the intermediate stage of vaginal microflora is much less investigated and characterized mainly due to the lack of definition of intermediate microflora and absence of appropriate methodology for its identification. As discussed by G. Donders in his comprehensive review of vaginal microflora "If Nugent were an ideal scoring system for bacterial vaginosis, with score 1-3 being normal and 7 being full-blown BV, score 4-6 should be transitional, partial or intermediate BV, but in reality it is not. Ideally this "intermediate flora" state represents a turning point from a normal state into BV, or from BV to normal. In reality, however, most of the women with so-called intermediate BV according to Nugent will have neither BV nor a normal flora."

As used herein, the term "abnormal vaginal microflora" refers to a microflora state that is associated with certain vaginal conditions or diseases. The most common alteration in vaginal microflora is a condition named Bacterial Vaginosis (BV). Abnormal vaginal microflora associated with BV has a number of distinct characteristics. The general feature of the abnormal microflora observed at BV is a replacement of *Lactobacillus* by fastidious anaerobic bacteria. Strong correlation of certain microbial species constituting abnormal vaginal microflora with BV condition defined by either Amsel criteria or Nugent score has been shown in multiple studies. Such microorganisms as *Gardnerella vaginalis, Atopobium vaginae, Megasphaera*, and BVAB2 frequently dominate abnormal vaginal microflora during the development of BV or transition towards BV condition.

As used herein, the term "pie chart" refers to a circular graph having radii dividing the circle into sectors proportional in angle and area to the relative size of the quantities represented.

As used herein, the term "profiling" refers to an assessment of the composition of the microbial species targeted by real-time PCR quantitative assays in a vaginal microflora. Each individual profile is represented as a graph reflecting relative concentrations of bacterial DNAs determined by real-time PCR quantitative assays.

As used herein, the term "predictive value" refers to the likelihood that a positive test result indicates disease, or that a negative test result excludes disease. "PPV" refers to a Positive Predictive Value. NPV refers to a Negative Predictive Value.

As used herein, the term "acoustic liquid dispenser" refers to an ATS-100 model of the Acoustic Transfer System manufactured by the EDC Biosystems, Fremont, Calif. and the like.

The present invention provides a real-time PCR quantitative detection assay for vaginal microflora including four (4) *Lactobacillus* species, as well as *Gardnerella vaginalis, Atopobium vaginae, Megasphaera* Type 1, *Megasphaera* Type 2 and BVAB2. The assay provides a diagnosis for bacterial vaginosis in humans; as well as diagnosing a woman with transitional vaginal microflora or normal vaginal microflora.

Real-Time PCR: Primers and Probes

Primer sets used in the present real-time PCR reactions may be prepared or obtained through commercial sources. For example, primer sets used in this invention can be commercially available from Abi (Foster City, Calif.). The primers used in the real-time PCR amplification preferably contain at least 15 nucleotides to 50 nucleotides in length. More preferably, the primers may contain 20 nucleotides to 30 nucleotides in length. One skilled in the art recognizes the optimization of the temperatures of the reaction mixture, number of cycles and number of extensions in the reaction. The amplified product (i.e., amplicons) can be identified by gel electrophoresis.

Aided with the help of DNA probe, the real-time PCR provides a quantum leap as a result of real-time detection. In real-time PCR assay, a fluorometer and a thermal cycler for the detection of fluorescence during the cycling process is used. A computer that communicates with the real-time machine collects fluorescence data. This data is displayed in a graphical format through software developed for real-time analysis.

In addition to the forward primer and reverse primer (obtained via commercial sources), a single-stranded hybridization probe is also used. The hybridization probe may be a short oligonucleotide, usually 20-35 bp in length, and is labeled with a fluorescent reporting dye attached to its 5'-end as well as a quencher molecule attached to its 3'-end. When a first fluorescent moiety is excited with light of a suitable wavelength, the absorbed energy is transferred to a second fluorescent moiety (i.e., quencher molecule) according to the principles of FRET. Because the probe is only 20-35 bp long, the reporter dye and quencher are in close proximity to each other and little fluorescence is detected. During the annealing step of the PCR reaction, the labeled hybridization probe binds to the target DNA (i.e., the amplification product). At the same time, Taq DNA polymerase extends from each primer. Because of its 5' to 3' exonuclease activity, the DNA polymerase cleaves the downstream hybridization probe during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, a Rotor-Gene System is used and is suitable for performing the methods described herein. Further information on PCR amplification and detection using a Rotor-Gene can conveniently be found on Corbett's website.

One of skilled in the art would conveniently optimize the design of primers and probes necessary for performing a real-time PCR in the detection of the selected microflora species present in vagina of a female. Preferably, a suitable primer utilizes the 5' exonuclease activity of thermostable polymerases such as Taq to cleave dual-labeled probes present in the amplification reaction.

The range of the primer concentration can also optimally be determined. The optimization involves performing a dilution series of the primer with a fixed amount of DNA template. The primer concentration may be between about 50 nM to 300 nM. An optimal primer concentration for a given reaction with a DNA template should result in a low Ct-(threshold concentration) value with a high increase in fluorescence (5 to 50 times) while the reaction without DNA template should give a high Ct-value. The PCR probes used are distinct from the PCR primers.

In one embodiment, the PCR probes may be dually-labeled with both a molecule capable of fluorescence and a molecule capable of quenching fluorescence. When the probes are intact, intra-molecular quenching of the fluorescent signal within the DNA probe leads to little signal. When the fluorescent molecule is liberated by the exonuclease activity of Taq during amplification, the quenching is greatly reduced leading to increased fluorescent signal. Non-limiting example fluorescent probes include 6-carboxy-flourescein moiety and the like. Exemplary quenchers include Black Hole Quencher 1 moiety and the like.

In another embodiment, suitable hybridization probes such as intercalating dye (e.g., Sybr-Green I) or molecular beacon probes can be used. Intercalating dyes can bind to the minor grove of DNA and yield fluorescence upon binding to double-strand DNA. Molecular beacon probes are based on a hairpin structure design with a reporter fluorescent dye on one end and a quencher molecule on the other. The hairpin structure causes the molecular beacon probe to fold when not hybridized. This brings the reporter and quencher molecules in close proximity with no fluorescence emitted. When the molecular beacon probe hybridizes to the template DNA, the hairpin structure is broken and the reporter dye is no long quenched and the real-time instrument detects fluorescence.

The probes and primers of the invention can be synthesized and labeled using well-known techniques. Oligonucleotides for use as probes and primers may be chemically synthesized according to the solid phase phosphoramidite triester method first described by Beaucage, S. L. and Caruthers, M. H., 1981, *Tetrahedron Letts.*, 22 (20): 1859-1862 using an automated synthesizer, as described in Needham-VanDevanter, D. R., et al. 1984, *Nucleic Acids Res.*, 12: 6159-6168. Purification of oligonucleotides can be performed, e.g., by either native acrylamide gel electrophoresis or by anion-exchange HPLC as described in Pearson, J. D. and Regnier, F. E., 1983, *J. Chrom.*, 255: 137-149.

In one embodiment, the real-time PCR may include the use of molecular beacon technology. The molecular beacon technology utilizes hairpin-shaped molecules with an internally-quenched fluorophore whose fluorescence is restored by binding to a DNA target of interest (See, e.g., Kramer, R. et al. *Nat. Biotechnol.* 14:303-308, 1996). Other suitable real-time PCR methods include the use of one or more hybridization probes, as determined by those skilled in the art. Exemplary probes such as the HEX channel and/or FAM channel probes, as understood by one skilled in the art.

Quantitation of Bacterial DNA by Real-Time PCR

One skilled in the art generally appreciates the literature regarding quantitation of DNA by PCR. For example, de Silva D, Wittwer C T. (2000) Monitoring hybridization during polymerase chain reaction. *J Chromatogr B Biomed Sci Appl.* 2000 Apr. 28; 741(1):3-13. Gibson, U E, Heid, C A, and Williams, P M (1996) A novel method for real time quantitative RT-PCR. *Genome Res* 6, 1095-1001. Lie, Y. S, and C. J., Petropoulos. (1998) Advances in quantitative PCR technology: 5' nuclease assays. Curr Opin Biotechnol 9 (1998): 43-48. Wittwer C T, Herrmann M G, Gundry C N, Elenitoba-Johnson K S. (2001) Real-Time Multiplex PCR Assays. *Methods.* 2001 December; 25(4):430-442.

There are two quantitative approaches to determine nucleic acid concentrations; namely, absolute qPCR or relative qPCR analysis. Absolute quantification relates the PCR signal to input copy number using a calibration curve; whereas relative quantitation measures the relative concentration of a nucleic acid against a known housekeeping gene (e.g., GAPDH or β-actin). Generally, both of these two strategies can be performed in real-time PCR.

In one embodiment, absolute quantitation by qPCR is used. This method requires the use of DNA standards such as DNA molecules of defined nucleotide content, length and concentration. These standards are applied to qPCR amplification using cycling conditions and reaction composition identical to those in qPCR of the interrogated sample. The pathogen DNA amplification signal in each of them is to be compared to the fluorescent output of three control reactions containing plasmid DNA with cloned targeted genes in known concentrations. Calibration curves may be conveniently built using a commercially available software (such as by the Bio-Rad CFX Manager software) after PCR amplification completion based on Ct scores of three control reactions. Control plasmids are used in the following concentrations: $10^7$ copies/µl, $10^5$ copies/µl and $10^3$ copies/µl. The absolute quantification of a pathogen DNA concentration (e.g., *Lactobacillus* or *Gardnerella*) can be performed automatically using Bio-Rad CFX Manager software in each of the PCR reactions.

In one embodiment, pathogen DNA standards can be chemically synthesized as oligonucleotides with known content and length. Alternatively, DNA control plasmids containing cloned fragments of exogenous DNA may also serve as standards for real-time PCR quantitation. Preferably, absolute qPCR quantitation by qPCR software requires the use of at least two DNA standards with known and different concentrations. Based on $C_t$ (cycle threshold) real-time PCR data, software generates a standard calibration curve of DNA concentrations that is used to determine initial concentration of DNA target in unknown samples.

In one embodiment, DNA control plasmids may be constructed for quantitation purposes by cloning corresponding PCR fragments into pCR2.1 vector using TOPO TA Cloning™ kit (Invitrogen Inc., Carlsbad, Calif.). PCR fragments of know composition may be conveniently obtained by performing PCRs with chromosomal DNAs of specific pathogens as templates.

In another embodiment, chromosomal DNA extracts from bacterial cultures purchased from ATCC (See, Table 2) may be used. Exceptions of this included PCR reactions with *Megasphaera* Type 1 and *Megasphaera* Type 2 for which no ATCC cultures are available. In yet another embodiment, DNA from clinical samples previously tested positive for these pathogens may also be used as templates for amplifications.

One skilled in the art would appreciate numerous standard DNA extraction processes. In one embodiment, the present plasmid DNA may be extracted using a ChargeSwitch®-Pro Plasmid Miniprep kit (Invitrogen Inc., Carlsbad, Calif.) and quantified with Fluoroskan Ascent microplate fluorometer (Thermo Fisher Scientific, Waltham, Mass.) with Quant-iT™ PicoGreen dsDNA reagent (Invitrogen Inc., Carlsbad, Calif.). All control plasmids were sequenced to confirm sequence identity in both directions using standard M13 primers and BigDye® Terminator v3.1 Cycle Sequencing on an Applied Biosystems 3130 genetic analyzer (Life Technologies, Carlsbad, Calif.).

In another embodiment, serial 10-fold dilutions of control plasmids with concentrations ranging from $0.4 \times 10^1$ to $0.4 \times 10^7$ copies per µl may be prepared by dilution of plasmid extracts with TE buffer. Control plasmids serial dilutions may be used in qPCR experiments to determine test sensitivities as well as run in parallel with vaginal samples as standards for quantitation purposes. Absolute initial amounts of targeted DNA in qPCRs may be calculated by the Bio-Rad CFX Manager software as Starting Quantities (SQ) on the basis of the Quantification Cycle (Cq) values.

Profiling of Vaginal Microflora

For purposes of the present invention, absolute initial amounts of bacterial DNA in qPCRs may be calculated by commercially available software such as Bio-Rad CFX Manager software.

In one embodiment, individual profiles representing relative concentrations of all nine pathogens targeted by qPCRs may be determined as follows:

a) Individual test results may be exported by Bio-Rad CFX Manager software as Microsoft Excel spreadsheets;

b) Data from all five PCRs (two (2) multiplex PCRs and three (3) uniplex PCRs) for nine (9) bacterial pathogens may be combined in a single Excel file containing individual sample information such as Amsel criteria values;

c) qPCR-derived data may be processed by software (e.g., Bio-Rad CFX Manager software) to generate sample-specific graphic outputs in form of pie-chart graphs;

d) Each of the sample-specific pie-chart graphs represent relative concentrations of DNAs of all nine (9) microbial pathogens corresponding to the relative concentrations of bacterial pathogens in OneSwab® clinical samples; and e) Excel spreadsheet qPCR data representation may be applied for the present study. This step may be omitted when massive data analysis of clinical samples is performed.

In one embodiment, each pie chart generated using the software shows pathogen-specific DNA in different colors or black and white patterns accompanied by corresponding percent values. In the event that relative concentration of specific pathogen is 0%, the corresponding color or black and white pattern does not present on the chart.

In one embodiment, the present invention provides three (3) uniplex qPCRs to quantify *Gardnerella vaginalis, Atopobium vaginae*, and BVAB2, respectively. The forward/reverse primers and fluorescently-labeled probes for each of the uniplex PCRs are species-specific and do not cross-react with other species.

In another embodiment, the present invention provides a multiplex PCR to simultaneously quantify *Lactobacillus jensenii, Lactobacillus gasseri, Lactobacillus iners* and *Lactobacillus crispatus*. A forward primer and a reverse primer are provided to target to amplify *Lactobacillus crispatus, Lactobacillus gasseri, Lactobacillus jensenii*, and *Lactobacillus iners. To differentiate these four (4) species, four (4) species-specific probes are provided.

In another embodiment, the present invention provides a multiplex PCR to quantify Megasphaera spp. A forward and a reverse primer coupled with species-specific probes are provided to target Megasphaera Type 1 and Megasphaera Type 2.

In one embodiment, the present invention provides a method of profiling the biological sample's relative amounts of Lactobacillus crispatus, Lactobacillus gasseri, Lactobacillus jensenii, Lactobacillus iners, Gardnerella vaginalis, Atopobium vaginae, Megasphaera Type 1 and Megasphaera Type 2, and BVAB2.

Although the utility of qPCR for characterization of vaginal microbiota is known, the present inventors provides quantitative feature of the qPCR, along with proper assay specificity and sensitivity, so as to ensure accurate identification of the targeted microbial species and assessment of their loads. One advantage of the present invention includes provides low price, short processing time and a closed-tube format predetermine wide acceptance of qPCR as a diagnostic tool. Another advantage of the present invention is that by focusing on a selected and limited number of microbial species typifying distinct vaginal communities, our research reveals a comparative analysis of qPCRs found to be adequate for assessing vaginal microflora status. The present assay hence provides a diagnostic tool in vaginal health.

In one embodiment, the present invention provides the choice of targeted microorganisms based, in part, on the advances in bacterial metagenomics and molecular characterizations of vaginal microbiota. The selected microflora includes five (5) BV-related bacteria: Gardnerella vaginalis, Atopobium vaginae, Megasphaera Type 1 and Megasphaera Type 2, and BVAB2, as well as four (4) dominant Lactobacillus species believed to play a protective role. These Lactobacillus species are found to be negatively associated with BV.

In one embodiment, the present inventors provide the quantitative power of using qPCR and its value in determining bacterial loads in vaginal milieu. One advantage of the present invention is to identify both qualitative and quantitative differences in microbial compositions between distinct sets of vaginal samples in normal women and women with BV. The present inventors discovered that there is a strong negative association between three (3) Lactobacillus species: Lactobacillus crispatus, Lactobacillus jensenii, Lactobacillus gasseri and BVAB. The negative association reaches 100% for these Lactobacillus microorganisms with Megasphaera and BVAB2. The lack of co-identification of these bacteria in vaginal compartment is one that is of qualitative difference as well as of quantitative difference. The observed mutual antagonism may be predetermined by the dissimilarities in optimal growth conditions, such as pH, as well as variety of biological active substances produced by lactobacilli that may serve as an explanation of reciprocal competitive exclusion of these groups of microorganisms demonstrated by qPCR.

In the present clinical study, we observed that healthy vaginal samples are often dominated by a single Lactobacillus species that is either Lactobacillus crispatus, Lactobacillus jensenii or Lactobacillus gasseri.

In the present invention, our clinical study reveals that, when BVAB species are present, they often have a high rate of co-existence. If BVAB are present, there is a depletion of Lactobacillus, demonstrating that BVAB and Lactobacillus species are mutually exclusive in the vaginal microflora environment.

The dynamic interactions between lactobacilli-dominated communities and BVAB populated communities are poorly known. Without wishing to be bound by a theory, it is speculated that BV is a disorder characterized by replacement of lactobacilli by BVAB. Culture-independent techniques suggest that changes in microbial composition occur during treatment of BV and BV relapse. Acquisition of bacterial vaginosis is strongly associated with a lack or loss of hydrogen peroxide producing lactobacilli. Therefore, it is speculated that hydrogen peroxide production is important in colonization resistance. A shift in vaginal flora from hydrogen peroxide-producing Lactobacillus species to anaerobes causes bacterial vaginosis. The lack of lactobacilli is accompanied by the increase of vaginal anaerobic bacteria. Women with this bacterial vaginosis have a large number of Gardnerella vaginalis, as well as many other organisms, in their vagina. High cytokines levels are associated with bacterial vaginosis in women.

Bacterial vaginosis poses as a risk factor for woman's health, such as preterm delivery. Treatment of bacterial vaginosis includes metronidazole, clindamycin, and phosphate vaginal cream. Lactobacillus acidophilus vaginal-probiotic containing oestriol (Prob) reduces bacterial vaginosis recurrence.

Physiological parameters such as menses, douching, and sexual activity have been proposed to be contributory factors in bacterial populations. Assuming the described microbial communities represent polar states of a common vaginal microbial "space", their reciprocal exclusivity observed in our study strongly suggest the existence of an "intermediate state" which would link these two polar states together.

The present clinical results provide an unexpected finding that Lactobacillus iners and Gardnerella vaginalis represent the two (2) dominant microflora species that are present in the "transitional state" (or "intermediate state") in vagina of women. Given little information is currently known, it is a surprising finding that the transitional microflora is characterized by the presence of Lactobacillus iners and Gardnerella vaginalis. The sum of relative amounts of Lactobacillus iners and Gardnerella vaginalis, when exceeding 50% of the total amount of the vaginal microflora, is indicative of a "transitional state." This information regarding the microflora composition provides a biomarker for transitional stage of vaginal pathology. The knowledge of transitional microflora composition should aid in the treatment of bacterial vaginosis. It also has an additional advantage of providing helpful information regarding re-occurrence incidence of bacterial vaginosis.

Based on the present clinical study, we discovered that Lactobacillus iners represents the most frequently identified bacterium in 58% of all vaginal samples examined. This data confirms its critical role of "ultimate adapter." Of interest is our observation that Lactobacillus iners was frequently detected in substantial concentrations in communities populated by BVAB. The decreased co-occurrence rate with other Lactobacilli is probably due to its less efficient amplification as compared with more abundant Lactobacillus species in our multiplex qPCR. It appears that Lactobacillus iners is a ubiquitous vaginal species which dominates many vaginal bacterial communities, as well as frequently making up its community. We observed substantial number of samples in which Lactobacillus iners was either the dominant or the only species identified. Based on this finding, we speculate that Lactobacillus iners' dominance, along with the depletion of other *Lactobacillus* species, indicates that the vaginal microflora may be in a transitional state.

*Gardnerella vaginalis* was a first bacterial species linked to bacterial vaginosis. Recent studies reveal its ubiquitous nature. Due to the common occurrence of this microorganism in healthy women, the role of *Gardnerella vaginalis* as a BV-associated marker has been challenged. In our clinical study, *Gardnerella vaginalis* was most frequently co-identified with Lactobacilli. *Gardnerella vaginalis* is found to be accompanied by either *Lactobacillus crispatus*, *Lactobacillus jensenii*, or *Lactobacillus gasseri* and it was found in 10% of all samples. 71% of *G. vaginalis*-positive samples contained *Lactobacillus iners*. Meanwhile the high frequency of co-existence with other BVAB indicates its distinct environmental preferences. Our clinical study clearly suggests a critical role of *Gardnerella vaginalis* as a transitional species between lactobacilli-dominated and BVAB-populated vaginal communities.

In one embodiment, the relative quantitative analysis of bacterial loads allows us to create profiling of vaginal microflora per individual (i.e., dividing all of the vaginal samples between three major groups: (i) microflora with numerical dominance of Lactobacilli; (ii) BVAB-dominated microflora; and (iii) intermediate microflora. The intermediate microflora group is formed on the basis of exclusion from the first and second groups. Our data indicates that the intermediate group is dominated by two microbial species; namely, *Lactobacillus iners* and *Gardnerella vaginalis*. We profile the vaginal microflora by applying our qPCR data analysis with respect to relative concentrations of bacterial species per individual woman. This allows us to differentiate the biological samples with presumably intermediate microflora from two groups of samples occupied by distinctly different communities representing normal and abnormal microflora types.

Bacterial markers of these communities and their association with clinical BV symptoms and BV diagnosis by conventional microbiological techniques can be established and characterized. The quantification and identification in clinical samples is sufficient for correct assignment (i.e., profiling) of the corresponding microflora states. Distinction of *Lactobacillus iners* and *Gardnerella vaginalis* as species associated with intermediate state of vaginal microflora is established. The intermediate state indicates *Lactobacillus iners* and *Gardnerella vaginalis* roles as a link or buffer between *Lactobacillus*-filled and BVAB-populated communities. Without wishing to be bound by a theory, we believe that *Lactobacillus iners* and *Gardnerella vaginalis* dominate the vaginal environment during the transition from normal to abnormal (aka BV) microflora. Vaginal samples used in our clinical study were characterized using Amsel scores. It is speculated that Nugent scores similarly may also permit the comparison of the suggested algorithm of qPCR data analysis with results obtained by conventional microbiological techniques.

It is of interest to note that we did not find dependence between median concentrations of target microorganisms determined by qPCR and clinical BV symptoms. Median concentrations of all tested bacteria were similar in the group with no BV (Amsel criteria 0-2) and the group with BV (Amsel criteria (3-4), even though the second group contained higher proportion of samples populated by BVAB comparing with the first group. We did observe a high variability in both bacterial DNA and human DNA concentrations in individual samples though which might be a consequence of different swabbing efficiency, DNA degradation during samples storing and shipping, or other factors.

We speculate that the relative quantitation of microbial species is appropriate and informative as compared to the absolute bacteria quantitation for purposes of vaginal microflora characterization especially using such medium as a vaginal swab.

In one embodiment, the present invention provides a set of five qPCRs targeting key bacterial species described as dominant in distinct vaginal communities. The present invention provides a strong negative association between two groups of microorganisms indigenous for vaginal microflora residing in two opposite states—normal and abnormal: a group of three *Lactobacillus* species: *Lactobacillus crispatus*, *Lactobacillus jensenii*, and *Lactobacillus gasseri* and a group of BV-associated pathogens: *Atopobium vaginae*, BVAB2 and *Megasphaera* Type 1 and II.

Based on the relative quantitative analysis of qPCR results, the present invention provides a third group of ubiquitous bacterial species presumably representing an intermediate state of vaginal microflora: *Lactobacillus iners* and *Gardnerella vaginalis*.

The following examples are provided to further illustrate various preferred embodiments and techniques of the invention. It should be understood, however, that these examples do not limit the scope of the invention described in the claims. Many variations and modifications are intended to be encompassed within the spirit and scope of the invention.

EXPERIMENTAL STUDIES

Example 1 Development and Validation of Respective qPCR Assay a) Selection of Specific Microflora Species for qPCR Assays We developed respective qPCR assays to quantify microflora that are present in vagina. We selected specific bacterial species in our study that is believed to represent a global vaginal microflora. This includes four (4) *Lactobacillus* species (namely, *Lactobacillus crispatus*, *Lactobacillus gasseri*, *Lactobacillus jensenii*, and *Lactobacillus iners*), *Gardnerella vaginalis*, *Atopobium vaginae*, *Megasphaera* Type 1 and *Megasphaera* Type 2, and BVAB2.

We established specific qPCR assays to quantify these selected microbial species present in vaginal samples. All DNA primers and fluorescently-labeled probes were designed in defined annealing temperature ranges to allow efficient amplification at the same thermal conditions and PCR chemical composition. Table 1 summarizes the general thermal conditions for the respective qPCR assays.

TABLE 1

Thermal Conditions for qPCRs

| Step | Time | Temperature | Basis |
|---|---|---|---|
| Hold | 2 min | 50° C. | UNG activity |
| Hold | 2 min | 95° C. | Inactivate UNG Activate platinum DNA polymerase Initial Denaturation |
| Cycling (35 cycles) | 10 seconds 45 seconds | 95° C. 60° C. | Denaturation Annealing & Extension Acquiring on FAM |

UNG means uracil N-glycosilase b) Uniplex PCR-qPCRs

In order to quantify *Gardnerella vaginalis*, *Atopobium vaginae*, and BVAB2 present in vaginal samples, we established three (3) separate qPCRs (i.e., 3 separate uniplex reactions). Each of the qPCRs utilizes species-specific primers and the corresponding fluorescent probes. For *Gardnerella vaginalis*, the developed qPCR utilizes a forward primer (SEQ ID NO: 7) and a reverse primer (SEQ ID NO: 8) as well as a fluorescent probe (SEQ ID NO: 9). For *Atopobium vaginae*, the developed qPCR utilizes a forward primer (SEQ ID NO: 1) and a reverse primer (SEQ ID NO: 2) as well as a fluorescent probe (SEQ ID NO: 3). For BVAB2, the developed qPCR utilizes a forward primer (SEQ ID NO: 4) and a reverse primer (SEQ ID NO: 5) as well as a fluorescent probe (SEQ ID NO: 6) (See, Table 2). The qPCRs were performed under thermal conditions as detailed in Table 1 above.

TABLE 2

DNA Primers and Fluorescently-Labeled Probes Used in qPCRs

| Target Organism | Primer/Probe | Sequence/Fluorophore | Conc. in PCR (nM) | Target Gene |
|---|---|---|---|---|
| *Atopobium vaginae* | Avag-tuf-S1 | AGACCTTCCTCCATAGCAATGGG (SEQ ID NO: 1) | 800 | Elongation factor |
| | Avag-tuf-AS1 | CCTCAGTTCTACTTCCGCACCAC (SEQ ID NO: 2) | 800 | EF1A |
| | Avag-tuf-TM1 | FAM-ACGTGGTCGCCAGGCATAGCC-BHQ1 (SEQ ID NO: 3) | 200 | |
| BVAB2 | BVAB 2 F6 | AAAACTCTTTGGACAGGGACGAAG (SEQ ID NO: 4) | 800 | 16s rRNA |
| | BVAB 2 R6 | CCAGCACTCAAGCTAAACAGTTTGT (SEQ ID NO: 5) | 800 | |
| | BVAB 2 Pr6 | CACTTATCTAGCCGCCTACACGCCC (SEQ ID NO: 6) | 200 | |
| *Gardnerella vaginalis* | GRO ES-7-F | GCAATCGCGTAGATGCGCTTGTTA (SEQ ID NO: 7) | 800 | Histidinol-phosphate |
| | GRO ES-7-R | GAAGTTTGCATACGGCTCGGCAAT (SEQ ID NO: 8) | 800 | transaminase |
| | GRO ES-7-Pr-1 | FAM-AGCGTAATCGCGTTGTAAGCGGTTTGC-BHQ1 (SEQ ID NO: 9) | 200 | |

We also have developed a qPCR assay to determine the presence of a human genetic target, namely GAPDH gene (as a reference house-keeping gene). This qPCR assay of GADPH gene was used for quality control purposes and to ensure that cervico-vaginal swabs were obtained from patients. The sequences for the primers and probes used are summarized in Table 3.

TABLE 3

DNA Primers and Fluorescently-Labeled Probes Used in qPCRs

| Target Organism | Primer/Probe | Sequence/Fluorophore | Conc. in PCR (nM) | Target gene |
|---|---|---|---|---|
| *Homo sapiens* | Human_GAPDH-F6 | GAGCACCAGGTGGTCTCCTC (SEQ ID NO: 10) | 800 | Glyceraldehyde-3-phosphate |
| | Human_GAPDH-R5 | CAGCCACATACCAGGAAATGAGC (SEQ ID NO: 11) | 800 | dehydrogenase |

TABLE 3-continued

DNA Primers and Fluorescently-Labeled Probes Used in qPCRs

| Target Organism | Primer/ Probe | Sequence/Fluorophore | Conc. in PCR (nM) | Target gene |
|---|---|---|---|---|
| Human_GAPDH-TM5 | HEX-CTGGCATTGCCCTCAACGACCACT-BHQ1 (SEQ ID NO: 12) | | 200 | | c) Multiplex PCR-qPCRs

To quantify *Lactobacillus* spp. and *Megasphaera* spp., we developed two (2) qPCRs that were multiplex reactions. These multiplex qPCRs have species-specific primers and fluorescently-labeled probes.

(i) *Lactobacillus* Multiplex PCR

We designed a multiplex PCR assay that can both quantify the amount of the microorganisms tested as well as differentiating the species within the *Lactobacillus* species. In other words, the multiplex qPCR for *Lactobacillus* can function to detect and speciation of the four (4) *Lactobacillus* species. In *Lactobacillus* multiplex qPCR, we designed a single pair of primers (i.e., a forward primer and a reverse primer) supplemented with four (4) species-specific probes that specifically target *Lactobacillus crispatus*, *Lactobacillus gasseri*, *Lactobacillus jensenii*, and *Lactobacillus iners*, respectively. The sequences for the primers and probes used are summarized in Table 4.

TABLE 4

DNA Primers and Fluorescently-Labeled Probes Used in qPCRs

| Target Organism | Primer/ Probe | Sequence/Fluorophore | Conc. in PCR (nM) | Target gene |
|---|---|---|---|---|
| *Lactobacillus*[1] | Lactob_tuf-S14 | CGTGGTTCAGCWTTGAAGGC (SEQ ID NO: 13) | 800 | Elongation factor Tu |
| | Lactob_tuf-AS20 | CTTCAACTGGCATYAAGAATGGC (SEQ ID NO: 14) | 800 | |
| *L. iners* | Lac.iners-TM | HEX-AGGCGATCCAGAACAAGAAGCAG-BHQ1 (SEQ ID NO: 15) | 100 | |
| *L. crispatus* | Lac.crispatus-TM | ROX-AGGCGACAAGGAAGCTCAAGAAC-BHQ2 (SEQ ID NO: 16) | 100 | |
| *L. gasseri* | Lac.gasseri-TM | FAM-AGGTGACCCAGAACAACAAGACG-BHQ1 (SEQ ID NO: 17) | 100 | |
| *L. jensenii* | Lac.jensenii-TM | Cy5-AGGTGACCCAGAACAAGAAAAGGT-BHQ2 (SEQ ID NO: 18) | 100 | |

(ii) *Megasphaera* Multiplex PCR

In *Megasphaera* multiplex qPCR, we designed a single pair of primers (a forward and a reverse) supplemented with two (2) species-specific probes that target *Megasphaera* Type 1 and *Megasphaera* Type 2. The sequences of primers and probes are provided in Table 5.

TABLE 5

DNA Primers and Fluorescently-Labeled Probes Used in qPCRs

| Target Organism | Primer/ Probe | Sequence/Fluorophore | Conc. in PCR (nM) | Target gene |
|---|---|---|---|---|
| Megasphaera[2] | Megasphaera cd F2 | CTTCCGCAATGGACGAAAGTCTG (SEQ ID NO: 19) | 800 | 16s rRNA |
| | Megasphaera cd R2 | CACGTAGTTAGCCGTGGCTTTC (SEQ ID NO: 20) | 800 | |
| Megasphaera Type 1 | Mega MP Probe 1 | FAM-CGGACGGATACTGTTGGCATCCGTC-BHQ1 (SEQ ID NO: 21) | 100 | |
| Megasphaera Type 2 | Mega MP Probe 2 | HEX-TGATGGCTATTTACCACCTTGCCG-BHQ1 (SEQ ID NO: 22) | 100 | |

The qPCR reaction performances were analyzed using serial dilutions of control plasmids with assay-specific cloned DNA sequences. Reaction efficiencies (E) varied between 95.7% and 110.2%, coefficients of correlation ($R^2$) were between 0.983 and 1.000, curve slopes varied between −3.100 and −3.428. Blank extracts with no sample or DNA added in the extraction process were used as no template controls (NTC). No false-positive responses were detected.

The specificities of the individual assays were confirmed against two sets of DNAs: *Lactobacillus* species (See, Table 6) and microorganisms indigenous to vaginal flora plus certain urogenital pathogens and human chromosomal DNA (See, Table 7). All the assays demonstrated excellent specificity detecting only corresponding microorganisms if they were available in our DNA sets. The only exception was nonspecific signal in *Lactobacillus* qPCR produced by *Lactobacillus gasseri* probe against *Lactobacillus johnsonii* DNA due to high level of DNA homology between these two species. There was no cross-reactivity of assays detected using set of control plasmids as PCR templates.

Assay accuracies were tested by sequencing per $10^1$ PCR fragments obtained from amplification of vaginal samples positive for specific pathogens and aligning sequences against GenBank data. All experimental sequences matched GenBank sequences.

The sensitivities of qPCR assays were established to be down to single DNA copies per reaction using serial dilutions of individual control plasmids. Multiplex tests were challenged with mixtures of the plasmids to simulate mixed communities of *Lactobacillus* species and *Megasphaera* species.

Biases towards the amplification of more abundant genetic targets were shown for both *Lactobacillus* qPCR and *Megasphaera* qPCR. When differences in concentrations of control plasmids exceeded $10^2$, less abundant targets failed to amplify. If control plasmids were mixed in equal concentrations there were no preferential amplifications of any targets in both multiplex tests. For clinical samples processing the limit of detection was set for $10^2$ DNA copies per PCR. Data having values below the threshold were excluded from the analysis.

Example 2 Clinical Study—Assessment of Vaginal Microflora by the Developed qPCR Assays We obtained a total of 186 vaginal swabs from females pursuant to our clinical study. All 186 swabs were tested positive for human DNA because they all contain human GAPDH gene. Out of the 186 cervico-vaginal samples, 17 of them failed to produce any qPCR signals. They were therefore considered to reflect an absence of vaginal microflora (i.e., lack of microbial species) under the present study. The other 169 cervico-vaginal samples were confirmed to test positive for qPCR signals, at least with respect to a microbial species out of the selected vaginal microflora (i.e., *Lactobacillus crispatus, Lactobacillus gasseria, Lactobacillus jensenii, Lactobacillus iners, Gardnerella vaginalis, Atopobium vaginae, Megasphaera* Type 1, *Megasphaera* Type 2 and BVAB2).

We used the qualitative qPCR results (i.e., the presence and absence) of these selected microbial species in determining the association between microbial species and clinical BV symptoms. Further, we used the quantitative qPCR results of these selected microbial species in assessing the relative amounts of bacterial DNAs per sample basis.

Our clinical study reveals that *Lactobacillus iners* was the most frequent microorganism identified in vaginal samples. In healthy women (n=135) (i.e., Amsel criteria 0-2), the frequency of *Lactobacillus iners* was found to be 50%, thus constituting the most frequent microbial species. The next frequent bacterial species after *Lactobacillus iners* in healthy cervicovaginal samples were *Lactobacillus crispatus* (33%) and *Gardnerella vaginalis* (30%).

In BV carriers (n=51) (i.e., Amsel criteria 3-4), the frequency of *Lactobacillus iners* was found to be 78%, thus constituting the most frequent microbial species in BV women. Contrary to that of healthy women, the next frequent bacterial species after *Lactobacillus iners* in BV carriers were *Gardnerella vaginalis* (69%) and *Atopobium vaginae* (67%).

Microflora Composition in Healthy Women and BV Carriers

The data from our clinical study clearly reveal that: (i) prevalence of microorganisms differed between normal women and women with BV; and (ii) the microflora difference was species-specific. For example, in healthy women, *Lactobacillus crispatus, Lactobacillus jensenii* and *Lactobacillus gasseri* were detected at a higher frequency. In contrast, women with BV have *Lactobacillus iners* present at a higher frequency. It is noteworthy to recognize that percentage of samples tested positive for BVAB was considerably higher in the BV group as compared to that of the healthy group (See, Table 8).

TABLE 8

Vaginal Microflora Composition in Clinically Characterized Swab Samples

| Bacterial Species/Vaginal Microflora | Amsel criteria 0-2 (135) | Amsel criteria 3-4 (51) |
|---|---|---|
| Lactobacillus[1] | 111 (82%) | 44 (86%) |
| L. crispatus | 44 (33%) | 7 (14%) |
| L. gasseri | 17 (13%) | 3 (6%) |
| L. jensenii | 23 (17%) | 7 (14%) |
| L. iners | 68 (50%) | 40 (78%) |
| BVAB | 45 (33%) | 37 (73%) |
| G. vaginalis | 41 (30%) | 35 (69%) |
| A. vaginae | 28 (21%) | 34 (67%) |
| BVAB2 | 18 (13%) | 22 (43%) |
| Megasphaera Type 1 | 22 (16%) | 22 (43%) |
| Megasphaera Type 2 | 4 (3%) | 7 (14%) |
| Normal microflora [3] | 62 (46%) | 12 (24%) |
| Intermediate microflora [3] | 28 (21%) | 6 (12%) |
| Abnormal microflora [3] | 27 (20%) | 31 (61%) |
| Mixed microflora [3] | 3 (2%) | 0 (0%) |
| Negative microflora [3] | 15 (11%) | 2 (4%) |
| Median number of bacterial species present | 1.96 | 3.47 |

[1]Samples positive for one or more of four Lactobacillus species: *L. crispatus*, *L. gasseri*, *L. jensenii* and *L. iners* were considered as Lactobacillus positive.
[2] Samples positive for one or more of five BV-associated pathogens: *G. vaginalis*, *A. vaginae*, BVAB2, *Megasphaera* Type 1, *Megasphaera* Type 2 were considered BVAB positive
[3] Vaginal microflora was defined as normal, intermediate, abnormal, mixed or negative according to qPCR results.

It is also noted that BV samples were co-infected (i.e., microorganisms co-exist in the same cervicovaginal samples) with higher number of microbial species as compared to that with normal samples: 1.96 against 3.47 per sample, respectively.

Relationship of Microbial Species within the Microflora Composition

Our clinical study also clearly reveals that there was an inverse correlation between a group of three *Lactobacillus* species: *Lactobacillus crispatus, Lactobacillus jensenii, Lactobacillus gasseri* and clinical BV symptoms (r=−0.311, P<0.001). Strong negative association was shown for these *Lactobacillus* species and BV-associated pathogens. For example, *Gardnerella vaginalis* and *Atopobium vaginae* were accompanied by *Lactobacillus crispatus, Lactobacillus gasseri*, or *Lactobacillus jensenii* in only 18 (10%) and 3 (2%) swabs respectively. None of the samples containing BVAB2 or *Megasphaera* was positive for these three *Lactobacillus* species. When samples were considered *Lactobacillus* positive if one or more of four *Lactobacillus* species: *Lactobacillus crispatus, Lactobacillus gasseri, Lactobacillus jensenii,* and *Lactobacillus iners* was present, there was weaker or no association between positivity for total lactobacilli and either clinical BV diagnosis (r=−0.192, P 0.021) or positivity for BVAB. (See, Table 9)

Similar percentage of both healthy individuals (82%) and BV carriers (86%) were colonized by Lactobacilli. *Lactobacillus iners* analyzed separately from other *Lactobacillus* species was positively associated with higher Amsel scores (r=0.165, P=0.001) and BVAB. Smaller number of *Lactobacillus iners*-positive samples was co-colonized by other *Lactobacillus* species comparing with BV-associated bacteria.

BVAB species demonstrated an increased rate of reciprocal co-infection (See, Table 6). 100% of *Megasphaera* Type 2-positive samples were also positive for *Gardnerella vaginalis, Atopobium vaginae*, and BVAB2.

Out of five (5) BV species *Gardnerella vaginalis* had lowest association rates with other BV pathogens. It was accompanied by other BVAB in 78% of *Gardnerella vaginalis*-positive samples and was the only BV-related microorganism in 22% of *Gardnerella vaginalis*-positive swabs. All BVAB were associated positively with *Lactobacillus iners* and negatively with other lactobacilli. There was a positive correlation between presence of BVAB and clinical diagnosis of BV (r=0.321, P<0.001). (See, Table 9)

Example 3 Profiling of Vaginal Microflora Per Individual

Quantitative analysis of bacterial loads demonstrated their high variability in the range between $10^1$ and $10^6$ genomic copies per reaction in both normal and BV specimens. However median concentrations of bacterial DNAs in both groups were similar for all tested bacteria: $10^4$-$10^5$ genomic copies per PCR depending on target microorganism (FIG. 1). Concentration of human chromosomal DNA was variable as well in the range between $10^1$ and $10^6$ genomic copies per reaction with the median concentration of $10^5$ genomic copies similar in both normal and BV qPCRs.

DNA concentrations for each of nine (9) pathogens determined by qPCRs were combined together generating pie chart graphs that represented the relative abundance of bacterial species in proportion to one another in each of the samples. Based on bacterial composition all of the samples were divided between three major groups presumably representing three states of vaginal microflora: normal, transitional and abnormal (See, FIG. 2).

(i) Normal Vaginal Microflora Profile

Microflora was considered normal when it was dominated by any one of three *Lactobacillus* species: *Lactobacillus crispatus, Lactobacillus gasseri*, and *Lactobacillus jensenii*, e.g., when total concentration of DNA of was at least 50% of total bacterial DNA derived as a sum of DNA concentrations of all species determined by qPCR. The rest of the bacterial DNA in normal samples was represented by two species: *Lactobacillus iners* and *Gardnerella. vaginalis*. Examples of Normal vaginal microflora pie charts are given below:

(ii) Abnormal Vaginal Microflora Profile

Vaginal microflora was considered abnormal when it was preoccupied by BVAB, e.g. total concentration of DNAs of BV-associated pathogens: *Atopobium vaginae, Megasphaera* and BVAB2 was 50% or higher of total bacterial DNA. The rest of microbial diversity in these samples was represented by *Lactobacillus iners* and *Gardnerella vaginalis*.

(iii) Transitional or Intermediate Vaginal Microflora Profile

Microflora was considered intermediate when two species: *Lactobacillus iners* and *G. vaginalis* demonstrated numerical dominance and sum of their DNA concentrations was more than a half of total bacterial DNA. The rest of bacterial DNA in intermediate samples was comprised by either members of lactobacilli group: *Lactobacillus crispatus, Lactobacillus gasseri*, and *Lactobacillus jensenii* or BV-associated bacteria: *Atopobium vaginae, Megasphaera* and BVAB2.

(iv) Mixed Microflora Profile

If samples contained mixtures of microorganisms from two groups: Lactobacilli group: *Lactobacillus crispatus, Lactobacillus gasseri*, and *Lactobacillus* jensenii or BV-associated bacteria: *Atopobium vaginae, Megasphaera* and BVAB2 in any combination and proportion they were referred as mixed microflora. Samples negative for all microorganisms tested were quoted as negative.

Both normal and abnormal microflora states determined by qPCR demonstrated correlation with clinical BV diagnoses (r=−0.286, P<0.001 and r=0.372, P<0.001 correspondingly). Percentage of samples with normal microflora was higher among healthy group whereas BV carriers' micro floras were more frequently characterized as abnormal (See, Table 5). Intermediate microflora had a weaker association (r=−0.087, P<0.001) with Amsel criteria. Median concentrations of bacterial DNAs in groups of samples divided according to bacterial dominance determined by qPCR results as described above showed both qualitative and quantitative differences (See, FIG. 1).

Example 4 Development of a Commercial Assay for the Multiplex qPCR

Acoustic liquid dispenser ("ADE") transfer liquid compounds from one plate to another, and it has been reported that ADE has utility in compound library screening. In this study, we apply ADE to a molecular diagnostic laboratory assay (i.e., qPCR). The following steps explain in detail of our developed commercial assay for multiplex qPCR.

a) Sample Identification

Cervical or cervico-virginal samples were collected using OneSwab® or Thin Prep (i.e., cervicovaginal scrapings used for Pap smears). The collected samples were subjected to accessioning and assigning a sequential identification number (i.e., logging the identification number into a computer system (also known as laboratory information system, LIS)).

b) DNA Extraction

We generated a XG sheet comprised of up to 96 specimens that would be extracted using a Qiagen X-tractor system (formerly produced by Corbett Robotics). The XG sheets are arranged in an 8×12 grid format, or 96 samples, which correspond to the layout of a 96 well plate. The designed XG sheets permits locating and physically assembling the biological specimens in a matching layout using customized large plastic trays that have holes in an 8×12 arrangement. The biological specimens are vortexed briefly and 150 microliters ($\mu$l) of each are withdrawn with a pipetteman and sterile tips and transferred to a sample block in the identical 8×12 grid format.

For controls, we added aliquots of a Canine Herpes virus Internal Control (CHVIC) to each of the specimens in the sample block (See, for example, van Doornum et al. J. Clinical Microbiol. 2003: 41(2): 576-80), the disclosure of which is incorporated herein by reference. Its purpose is to serve as a Quality Control mechanism that verifies that the extraction procedure itself was successful. Elution of the DNA from a thoroughly washed membrane with 80 $\mu$l of a Tris-based solution into an elution tube which has a 2D barcode imprinted on the bottom. These tubes are arranged in the same 8×12 format as the sample block and the 2D barcodes had previously been imported into the Laboratory Information System. The LIS maintains the connection between the specimen identification number and the 2D barcode on the elution tube.

Each biological specimen can be extracted a total of four (4) times. Possible reasons for re-extracting a biological specimen (represented by the 2D barcode tube) are failed extractions (including equipment failure or incomplete/absent elution buffer in the 2D barcode tube) or the presence of a DNA inhibitor (determined by a reduction or complete absence of CHVIC detected in an upcoming real-time PCR assay). At this point, the XG plate was processed; failed specimens were marked for re-extraction.

c) ADE (Aoustic Droplet Ejector) Plate (384 Well) Setup

Each 2D barcode tube contains 80 $\mu$l of the DNA material. 9 $\mu$l was withdrawn and combined with 3 $\mu$l DMSO in a 384 well (ADE; Acoustic Droplet Ejector) plate. The workflow permitted this process to be performed using a CAS4800 liquid handling system (8 tip head) or a Biomek FX liquid handling system (96 tip head). The latter is significantly faster and can be used to prepare a single ADE plate from one, two, three, or four full 96 tube extraction sheets. The former has more flexibility and can be used to combine up to 10 partial XG sheets into one 384 well plate (as long as the total number of samples does not exceed 384).

Our commercial assay provides the operator with the ability to toggle back and forth between the two liquid Transfer Options. Once One Pathway is Selected (Based Upon full/partial plates, number of plates, availability of machines), our assay would create the appropriate data files directing the transfer process. Once the actual physical transfer was competed, the system operator could process the sheet and the ADE plate was finalized and available for use.

d) CONTROL (CON) Plate Setup

CON plates contain the High ($2\times10^6$ copies/$\mu$l) plasmid, Medium ($2\times10^4$ copies/$\mu$l) plasmid, Low ($2\times10^2$ copies/$\mu$l) plasmid, and NTC controls (i.e., No Template Control) to be incorporated into each assay. The plates were 384 well acoustic plates that were divided into 4×96 well grids, each of which would contain 9 $\mu$l of the control material (plasmid DNA control) and 3 $\mu$l of DMSO. The quantity of plasmid material was provided and fixed. A profile for the CAS4800 liquid handling system was also created by to permit this process of physically adding the components. Components could also be added manually with a pipetteman and pipette tips.

Plates were sealed and stored at 4° C. between uses. Volumes of each well on the plate were tracked and would be treated as failed automatically if (a) the volume fell below 3 $\mu$l, (b) there is a contamination in an NTC, or (c) the operator chose to specifically fail a selected well or the entire plate.

e) PCR Set Up

All PCRs were run by the traditional (XL-20, CAS4200N or CAS4800, RotorGene 3000/6000) system. Select PCRs could be run by the Acoustic method (EDC ATS-100, BioRad 384CFX).

Acoustic PCRs (AcPCRs) can be run before, simultaneously, or after the CHVIC PCR. If AcPCRs are run before the CHVIC assay, results are put on a hold until the CHVIC assay has been deemed successful on that particular extraction. If the CHVIC fails but one or more of the AcPCR has been completed, it would still be reprocessed and those AcPCRs that were run would be repeated.

For tradition PCR, sheets can be produced using a variety of interfaces that included Virtual PCRs, PHArA (Pragmatic Heuristic AutomatedAnalyzer), and TCI Assembly Sheets. TCI Sheets were generated to assemble the 2D barcode tubes using the XL20 tube sorting machines (BioMicroLab, Cocord, Conn.). TCI Sheets contain the origination plate and location, the destination plate and location, the barcode and number designation of the specimen, and the test(s) to be performed on each line. This file was loaded onto the XL-20 and the program initiated. The system operators collect the source plates and load them onto the XL-20 and it will pick each up in turn, verify the 2D barcode on the tube matches that in the file, and place it into the appropriate destination plate. Depending upon the fragmentation of the bar-coded tubes across plates, the operators may have to locate and swap in multiple plates to complete the process.

Two liquid handlers were available—the CAS 4200N and the CAS 4800. The former has a single pipette head and was capable of cherry picking (specifically select single samples from source plates) while the latter has an eight channel pipette head and was only usable if all eight positions in the column are to have the same test performed. According, the CAS 4800 was significantly faster than the CAS 4200N.

Once the target plates have been assembled on the XL20 machines, they were transferred to an operator that would set up the assays on the appropriate CAS instrument. The source plates were positioned into the instrument in locations designated on the TCI Sheet and also in the CAS4 generated template file created through another computer program (TrimCor). The CAS4 file contains the instructions that the CAS instruments (CAS4200N or CAS4800) use to operate.

Plasmid controls (high, medium, low, and NTC) for each assay were also positioned on the deck. Mastermix for the assays contained primers, probes, buffers, stabilizers, and enzymes (Taq polymerase and Uracil N-glycosylase) to perform the PCR. These were either prepared in advance or immediately prior to use. Pipette tips were replenished. The process was initiated and master-mix and nucleic acid extractions from source samples were transferred into tubes and mixed. The tubes were capped and transferred to the machines for PCR analysis.

Each assay has its own particular template defining run times, temperatures, and numbers of cycles. The source tubes were capped. At the conclusion of the PCR runs, a laboratory technician interpreted the results, including verifying that all positive controls amplified and the NTC did not. Positive specimens were clearly marked on a PCR worksheet and the worksheet and printed interpretation are passed to the Quality Control staff to perform their own analysis.

For acoustic PCRs set up, we used the EDC ATS-100 dispensers and then analyzed on the BioRad CFX384 thermocyclers. Source plates consisted of ADE plates containing nucleic acid extracted patient specimens (9 µl specimen and 3 µl DMSO) or CON plates which contain plasmid control material (high, medium, low, NTC; all with a ratio of 3:1 plasmid:DMSO). Worksheets were created and could contain a maximum of 368 samples and 16 controls. Worksheets were named for the destination target plate (deemed the CFX plate) and contain the source plates, source locations, and source identifications of the samples. The CFX plates contain master-mixes specific for each assay that contain primers, probes, buffers, stabilizers, and enzymes (Taq and Uracil N-glycosylase). These plates are prepared in advance and are stored at 4° C. until use.

The initial assays included CHVIC [an internal extraction control], *Atopobium vaginae*, BVAB2, *Gardnerella vaginalis*, *Megasphaera* Types I and II (duplex assay), and *Lactobacillus* (quadraplex assay).

Target plates were removed from 4° C., centrifuged, and the adhesive plate seals were removed. Each plate was processed individually and only when required by instrumentation. The plates were next loaded onto the ATS-100 dispenser that scanned the barcode located on the side of the plate. The operator then prompted to load the required source plates. Each must be centrifuged and de-sealed before loading onto the machine; it was then prompted to continue. After the ATS-100 was finished with an ADE or CON plate, each was immediately resealed and returned to 4° C.

Once all ADE and CON plates have been loaded, the CFX plates was sealed, quickly spun in a plate centrifuge, and placed into the BioRad 384CFX instrument for analysis.

f) Statistical Report

The qPCR results were provided in statistical reports designed to optimally use the overall system. These reports could be used to determine turnaround times, percent test and specimen completion, those specimens which can be completed with a minimal number of tests to be performed, optimal combinations of tests to run, suggestions for the next best action to perform (PHArA), and workflow warnings that would impact individual specimens or the overall process.

g) Quality Control Enhancements

Several enhancements have been added to the Quality Control procedures for Acoustic PCR tests. These include: Blind Interpretations—In the traditional laboratory workflow, once a RotorGene instrument run had been completed, a laboratory technician performed an initial interpretation of the results. All three positive and negative controls were verified to have generated the expected results and patient specimens are marked as positive or negative based upon the amplification curves. If a particular curve was suspect or ambiguous, the laboratory technician would mark that specimen as a 'Redo' and the assay can be repeated. This paperwork was then transferred to the Quality Control/ Quality Assurance department whereby the raw data is reanalyzed and the initial interpretation is checked; the Quality Control department makes the final call for patient results.

The Acoustic Workflow was markedly different. Initially after the EDC acoustic dispenser has completed its run, a data file was imported into the LIS and the volume of each and every well was updated; if there were spotting errors, the PCR record is marked and that assay would be repeated following commitment of the PCR sheet.

Example 5 Application of Acoustic Liquid Dispenser to the Commercial Assay

In this study, we utilized an Acoustic Liquid Dispenser system in our Commercial Assay as detailed above in Example 4.

We performed a side-by-side comparison of our developed commercial *Lactobacillus* qPCR test. A total of 184 clinical OneSwab® samples were subjected to DNA extraction and qPCRs in duplicate. qPCR reactions were assembled and performed in two different format as follows:

a) Manual DNA dispensation format (i.e., qPCR volume 15 µl)

b) Acoustic DNA dispensation format (i.e., qPCR volume 4 µl)

The main purpose of this study was to obtain a reproducible result using acoustic liquid dispenser (as compared to that of manual dispenser). In this regard, manual DNA dispensation was performed using Labnet multichannel pipette following our *Lactobacillus* qPCR assay. Total DNA volume added to 15 µl qPCR was 2.5 µl per reaction. In contrast, acoustic DNA dispensation was performed using an EDC Biosystems ATS-100 Acoustic Droplet Ejector instrument. Total DNA volume added to each 4 µA qPCR was 0.5 µA per reaction.

qPCRs in manual DNA dispensation format were performed twice and qPCR results were averaged. qPCRs in acoustic DNA dispensation format were performed six times with following qPCR designations: 711447, 711450, 745161, 745162, 745163, 745173.

Comparative statistical analysis of qPCR results was performed using computer software that utilizes a 2-way contingency table analysis. Results are summarized in the following Table 9. A high correlation is observed between manual qPCR runs and acoustic qPCR runs. We concluded from these experiments that:
a) *Lactobacillus* multiplex qPCR performance testing has demonstrated high reproducibility, accompanied by low run-to-run variations, no false-positive and low number of false-negative results.
b) Comparative analysis of the manual and acoustic DNA dispensation approaches reveals that both qPCRs have high sensitivity, specificity, positive predictive value, and negative predictive values.

TABLE 9

Sensitivity, Specificity, Positive Predictive Value, and Negative Predictive Value of Acoustic DNA Dispensation Against Manual DNA Dispensation in *Lactobacillus* qPCR

|  | PCR # | Sensitivity | Specificity | PPV | NPV |
|---|---|---|---|---|---|
| *Lactobacillus* gasseri | 711447 | 0.8947 | 0.9818 | 0.85 | 0.9878 |
|  | 711450 | 0.9211 | 0.9788 | 0.8333 | 0.9908 |
|  | 745161 | 0.9444 | 0.9785 | 0.8293 | 0.9938 |
|  | 745162 | 0.9189 | 0.969 | 0.7727 | 0.9905 |
|  | 745163 | 1 | 0.9544 | 0.6939 | 1 |
|  | 745173 | 0.8947 | 0.9814 | 0.85 | 0.9875 |
|  | Average | 0.928967 | 0.973983 | 0.804867 | 0.991733 |
| *Lactobacillus* jensenii | 711447 | 0.9375 | 0.9375 | 0.7595 | 0.9862 |
|  | 711450 | 0.9219 | 0.9441 | 0.7763 | 0.9829 |
|  | 745161 | 0.8033 | 0.9529 | 0.7778 | 0.9593 |
|  | 745162 | 0.8 | 0.9558 | 0.7869 | 0.959 |
|  | 745163 | 0.9194 | 0.9172 | 0.6951 | 0.9823 |
|  | 745173 | 0.7969 | 0.9373 | 0.7286 | 0.9562 |
|  | Average | 0.863167 | 0.9408 | 0.754033 | 0.970983 |
| *Lactobacillus* iners | 711447 | 0.9946 | 0.8261 | 0.8512 | 0.9935 |
|  | 711450 | 1 | 0.8424 | 0.8638 | 1 |
|  | 745161 | 0.9945 | 0.8247 | 0.8702 | 0.9922 |
|  | 745162 | 0.9835 | 0.8118 | 0.8483 | 0.9787 |
|  | 745163 | 0.9891 | 0.8204 | 0.8578 | 0.9856 |
|  | 745173 | 0.9781 | 0.8263 | 0.8606 | 0.9718 |
|  | Average | 0.989967 | 0.825283 | 0.85865 | 0.986967 |
| *Lactobacillus* crispatus | 711447 | 1 | 0.9704 | 0.9245 | 1 |
|  | 711450 | 1 | 0.9667 | 0.9159 | 1 |
|  | 745161 | 1 | 0.962 | 0.9074 | 1 |
|  | 745162 | 1 | 0.9511 | 0.8829 | 1 |
|  | 745163 | 0.9898 | 0.9537 | 0.8899 | 0.996 |
|  | 745173 | 0.9898 | 0.944 | 0.8661 | 0.9961 |
|  | Average | 0.9966 | 0.957983 | 0.897783 | 0.998683 |

Example 6 Analysis of Vaginal Mucosal Immune Markers in Healthy and BV Patients

Figure 4B:
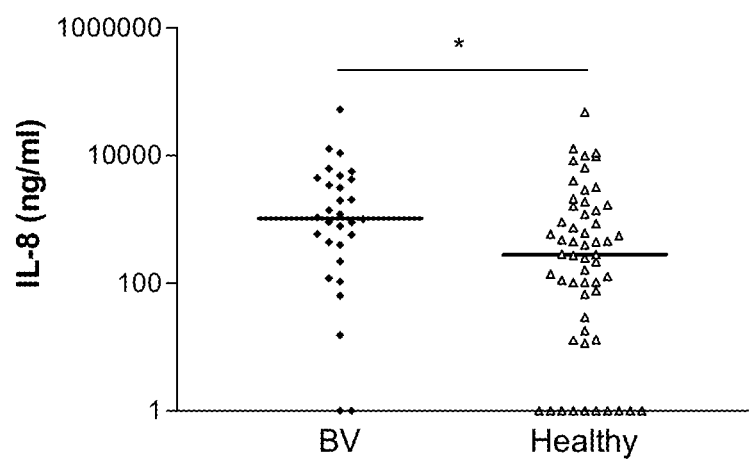
Figure 4C:
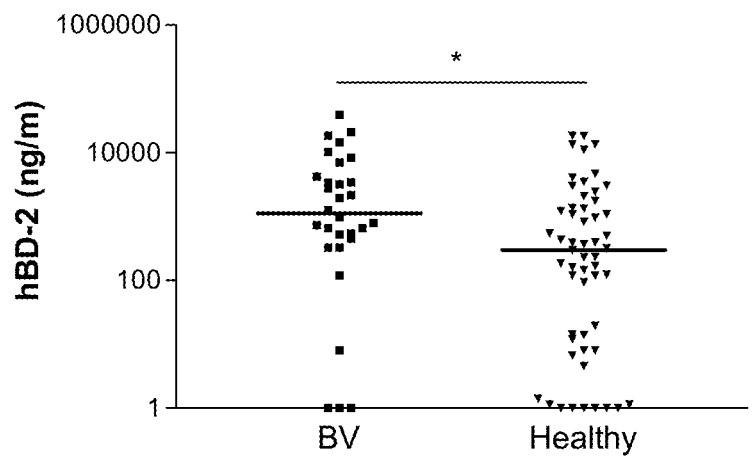
Figure 4D:
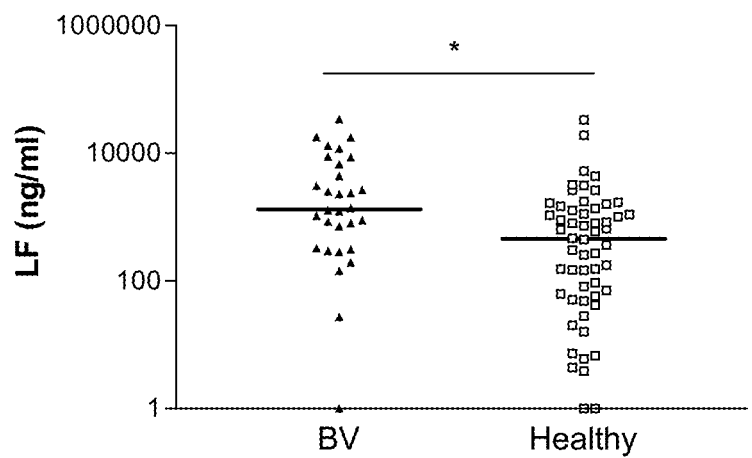
Figure 5A:
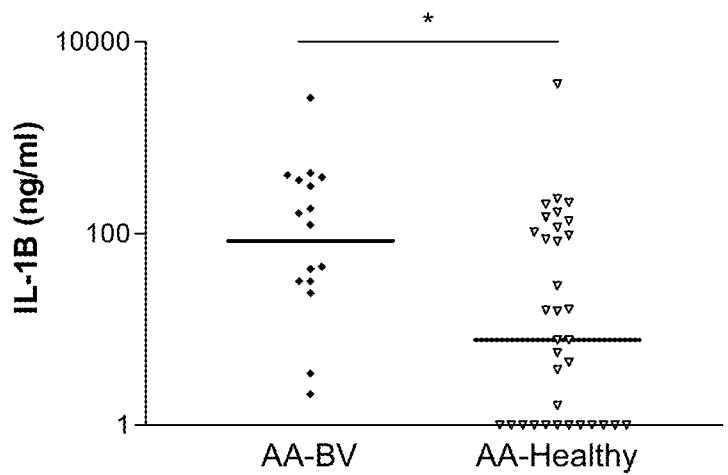
FIG. 5a, FIG. 5b, FIG. 5c and FIG. 5d depict vaginal levels of (a) interleukin-1 beta (IL-1$\beta$), (b) interleukin-8 (IL-8), (c) human beta-defensin 2 (hBD-2) and (d) lactoferrin (LF), among healthy and BV African American patients. Horizontal bar indicates median value for each column. * $P<0.05$, ** $P<0.01$, Mann-Whitney U Test.
Figure 5B:
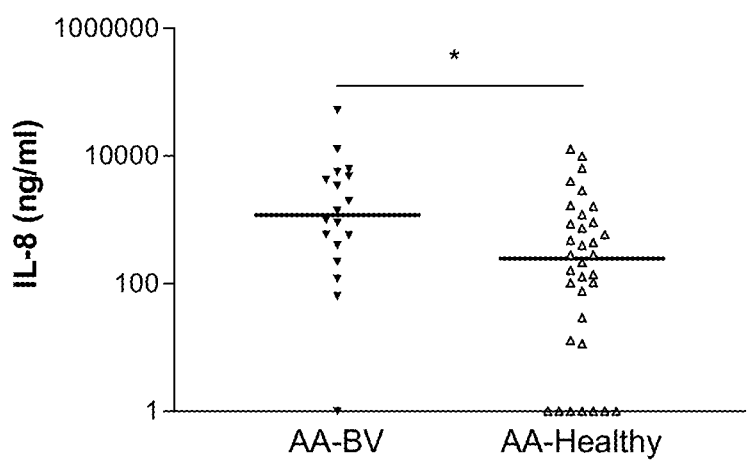
Figure 5C:
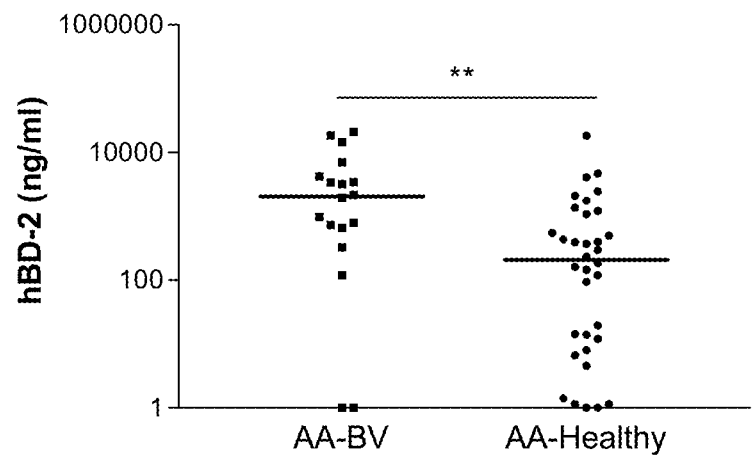
Figure 5D:
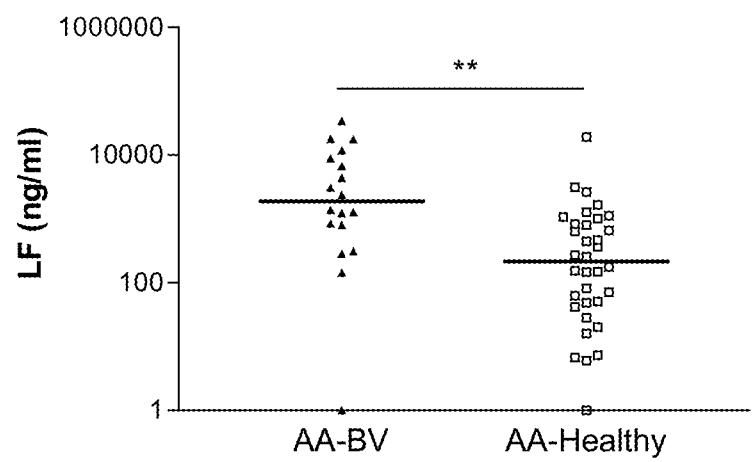

Transport medium from OneSwab® vaginal specimens was assayed by ELISA for interleukin-1 beta (IL-1β), interleukin-8 (IL-8), human beta-defensin 2 (hBD-2) and lactoferrin (LF). When comparing BV and healthy patients, we observed statistically significant elevation of all four immune markers (FIGS. 4a-4d respectively). The median values for IL-1β (P=0.034) among BV and healthy patients were 44 ng/mL and 9 ng/ml, respectively (FIG. 4a). The median values for IL-8 (P=0.016) among BV and healthy patients were 1,037 ng/mL and 282 ng/mL, respectively (FIG. 4b). The median values for hBD-2 (P<=0.010) among BV and healthy patients were 1,118 ng/mL and 297 ng/mL, respectively (FIG. 4c). The median values for LF (P=0.0019) among BV and healthy patients were 1,326 ng/mL and 456 ng/mL, respectively (FIG. 4d) (P values determined by Mann-Whitney U Test).

Because race may play a role in the composition of the vaginal flora and BV susceptibility (See, Royce et al., *Sex. Transm. Dis.*, 1999, Vol. 26, No. 2, pp. 96-102), we analyzed the data for African American patients as a separate cohort (FIGS. 5a-5d). In the African American population, all four immune markers were significantly different between BV and healthy patients, with median values of 84 ng/mL and 8 ng/mL, respectively for IL-1β (P=0.017) (FIG. 5a), 1,195 ng/mL and 248 ng/mL, respectively for IL-8 (P=0.012) (FIG. 5b), 2,053 ng/mL and 209 ng/mL, respectively for hBD-2 (P=0.0051) (FIG. 5c), and 1,883 ng/mL and 216 ng/mL, respectively for LF (P=0.0006) (FIG. 5d) (P values determined by Mann-Whitney U Test).

Figure 6A:
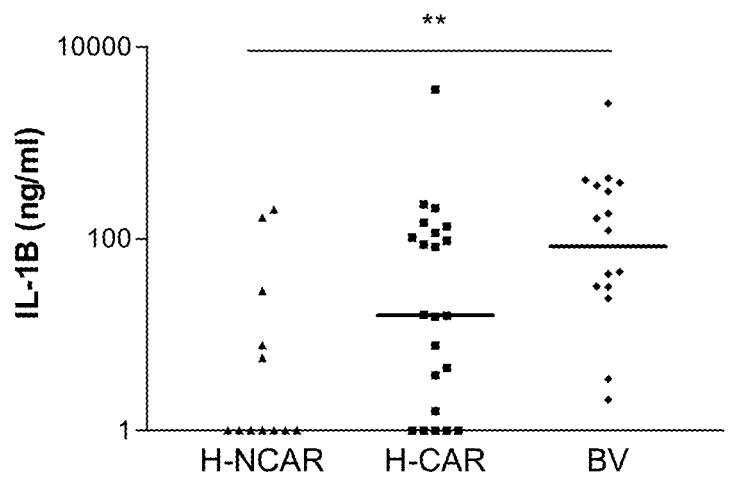
FIG. 6a, FIG. 6b, FIG. 6c and FIG. 6d depict vaginal levels of (a) interleukin-1 beta (IL-1$\beta$), (b) interleukin-8 (IL-8), (c) human beta-defensin 2 (hBD-2) and (d) lactoferrin (LF), among healthy non-carrier (H-NCAR), healthy carrier (H-CAR) and BV African American patients. Horizontal bar indicates median value for each column. The median value for H-NCAR in FIG. 3a is 0. * $P<0.05$,  $P<0.01$, * $P<0.001$, Mann-Whitney U Test.
Figure 6B:
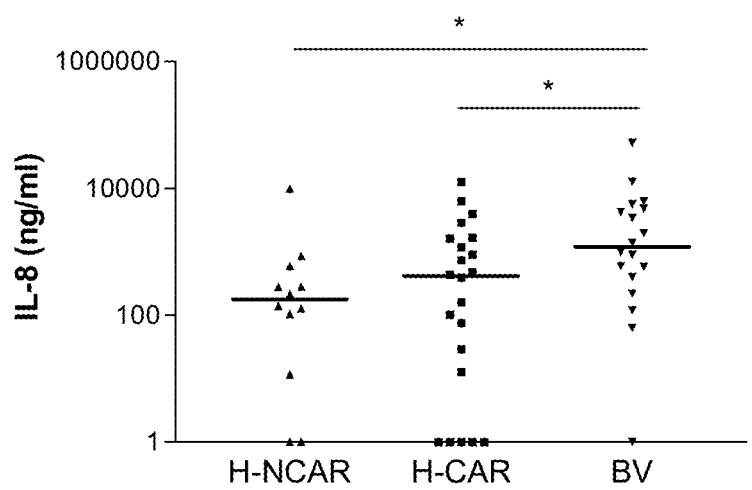
Figure 6C:
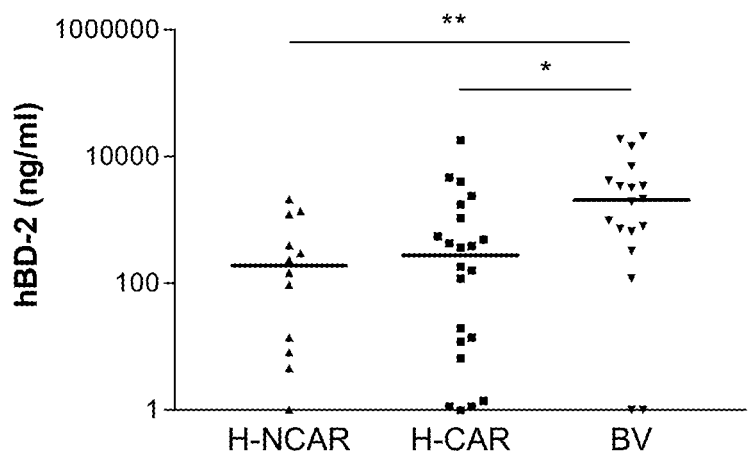
Figure 6D:
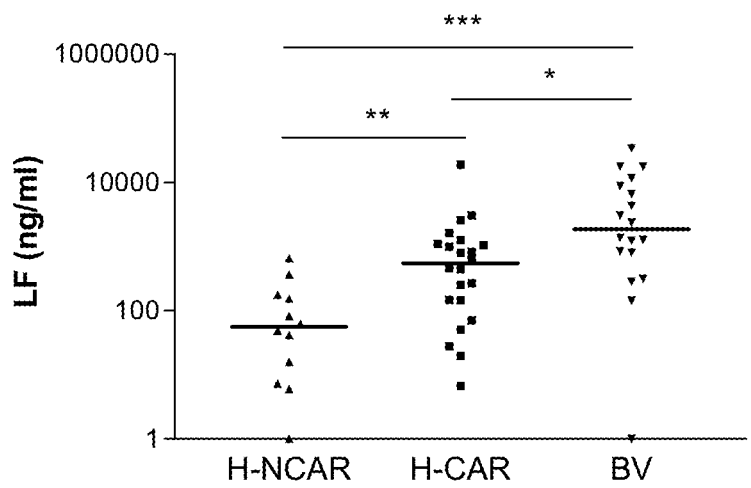

When healthy non-carrier (H-NCAR) were compared to healthy carrier (H-CAR) and BV African American patients, similar differences among the four (4) immune markers were observed (See, FIG. 6a (IL-1β), FIG. 6b (IL-8), FIG. 6c (hBD-2) and FIG. 6d (LF)).

When analyzed for Caucasian patients however, we did not observe any statistically significant differences between BV and healthy patients, with median values for BV and healthy patients of 37 ng/mL and 16 ng/mL, respectively for IL-1β, 993 ng/mL and 451 ng/mL, respectively for IL-8, 601 ng/mL and 831 ng/mL, respectively for hBD-2, and 969 ng/mL and 1,000 ng/mL, respectively for LF (data not shown).

Experimental Methods and Procedures

A. Real-Time PCR Assay for *Megasphaera* Type 1 & 2

The present real-time PCR assay provides a rapid, specific and sensitive detection of *Megasphaera* type 1 and 2. Biological sample, such as cervical swab, is obtained (e.g., via OneSwab). DNA is isolated using QIAamp DNA Mini Kit from Qiagen. The following primers were constructed commercially from IDT Technologies:

| Primer | Sequence 5' to 3' | Location | Product |
|---|---|---|---|
| Megasphaera cd F2 | 5'-CTT CCG CAA TGG ACG AAA GTC TG-3' (SEQ ID NO: 19) | 16S rRNA gene | 154 bp |
| Megasphaera cd R2 | 5'-CACGTAGTTAGCCGTGGCTTT C-3' (SEQ ID NO: 20) |  |  |
| Mega MP Probe 1 | /56-FAM/CGGACGGATACTGTTGGCATCCG TC/3BHQ_1/ (SEQ ID NO: 21) |  |  |
| Mega MP Probe 2 | /5HEX/TGATGGCTATTTACCACCTTGCCG /3BHQ_1/ (SEQ ID NO: 22) |  |  |

PCR reactions are performed in 15 µl reaction volumes using the following PCR parameters:

| Component | Stock | Aliquot Volume | Final Concentration |
|---|---|---|---|
| Extracted DNA | 20 ng/µL | 2.5 µl | 2 ng/µL |
| AccuQuant ™ Custom SuperMix* | 2X | 7.5 µl | 1X |
| *Megasphaera* cd F2 | 10 µM | 1.2 µl | 800 nm |
| *Meagasphaera* cd R2 | 10 µM | 1.2 µl | 800 nm |
| Mega MP Probe 1 | 10 µM | 0.225 µl | 150 nM |
| Mega MP Probe 2 | 10 µM | 0.225 µl | 150 nM |
| Nuclease free H$_2$O | | 2.15 µl | |

*2x reaction buffer containing dNTP/dUTP, iTaq, MgCl$_2$, UNG, and stabilizers.

Four tubes are reserved for controls. The positive controls are to be diluted from the *Megasphaera* type 1 & 2 plasmid (pMega1CD and pMega2CD) and consist of the following:

| Control | Concentration | Final Copies in the Reaction |
|---|---|---|
| M1 + M2 Positive High | 100,000,000 copies/µl | 10,000,000 |
| M1 + M2 Positive Middle | 1,000,000 copies/µl | 100,000 |
| M1 + M2 Positive Low | 10,000 copies/µl | 1,000 |
| NTC | N/A | 0 |

*Megasphaera* type 1 & 2 positive controls are prepared from a $10^8$ copies/µl plasmid stock. Real-Time PCR run programming and its profile conditions are carried out by the following steps:

| Step | Time | Temperature | Reason |
|---|---|---|---|
| Hold | 2 minutes | 50° C. | UNG activity |
| Hold | 5 minutes | 95° C. | Inactivate UNG Activate DNA polymerase Initial Denaturation |
| Cycling (40 cycles) | 10 seconds | 95° C. | Denaturation |
| | 45 seconds | 60° C. | Annealing & Extension Acquiring on FAM |

B. Real-Time PCR on Bio-Rad CFX for *Atopobium vaginae*

The present real-time PCR assay using Bio-Rad CFX (real-time PCR instrument from Bio-Rad) provides a rapid, specific and sensitive detection of *Atopobium vaginae*. Biological sample, such as cervical swab, is obtained (e.g., via OneSwab). DNA is isolated using QIAamp DNA Mini Kit from Qiagen. The following primers were constructed commercially from IDT Technologies:

| Primer | Sequence 5' to 3' | Location | Product |
|---|---|---|---|
| Avag-tuf-S1 | AGACCTTCCTCCATAGCAATGGG (SEQ ID NO: 1) | Elongation factor Tu | 149 bp |
| Avag-tuf-AS1 | CCTCAGTTCTACTTCCGCACCAC (SEQ ID NO: 2) | (tuf gene) | |
| Avag-tuf-TM1 | /56-FAM/ACGTGGTCGCCAGGCATAGCC/3BHQ_1/ (SEQ ID NO: 3) | | |

PCR reactions are performed in 15 µl reaction volumes using the following PCR parameters:

| Component | Stock | Aliquot Volume | Final Concentration |
|---|---|---|---|
| Extracted DNA | 20 ng/µl | 2.5 µl | 2 ng/µl |
| Biorad qPCR Mastermix * | 2X | 7.5 µl | 1X |
| Avag-tuf-S1 | 10 µM | 1.2 µl | 800 nM |
| Avag-tuf-AS1 | 10 µM | 1.2 µl | 800 nM |
| Avag-tuf-TM1 | 10 µM | 0.3 µl | 200 nM |
| H2O | | 2.3 µl | |

* 2x reaction buffer containing dNTP/dUTP, iTaq, MgSO$_4$, UNG, and stabilizers.

Four tubes are reserved for controls. The positive controls are to be diluted from the *Atopobium vaginae* vector pAvagSB1 and consist of the following:

| Control | Concentration | Final Copies in the Reaction |
|---|---|---|
| Positive High | 100,000,000 copies/µl | 10,000,000 |
| Positive Middle | 1,000,000 copies/µl | 100,000 |
| Positive Low | 10,000 copies/µl | 1,000 |
| NTC | N/A | 0 |

Program of a real-time PCR run, and its profile conditions are carried out by the following steps:

| Step | Time | Temperature | Reason |
|---|---|---|---|
| Hold | 2 min | 50° C. | UNG activity |
| Hold | 2 min | 95° C. | Inactivate UNG Activate platinum DNA polymerase Initial Denaturation |
| Cycling (35 cycles) | 10 seconds | 95° C. | Denaturation |
| | 45 seconds | 60° C. | Annealing & Extension Acquiring on FAM |

C. Real-Time PCR Assay on Bio-Rad CFX for BVAB2

The present real-time PCR assay using Bio-Rad CFX provides a rapid, specific and sensitive detection of BVAB2. Biological sample, such as cervical swab, is obtained (e.g., via OneSwab). DNA is isolated using QIAamp DNA Mini Kit from Qiagen. The following primers were constructed commercially from IDT Technologies:

| Primer | Sequence 5' to 3' | Location | Product |
|---|---|---|---|
| BVAB2 F3 | AAAACTCTTTGGACAGGGACGAAG (SEQ ID NO: 4) | 16S rRNA | 266 bp |
| BVAB2 R3 | CCAGCACTCAAGCTAAACAGTTTGT (SEQ ID NO: 5) | gene | |
| BVAB2 Pr | CACTTATCTAGCCGCCTACACGCCC (SEQ ID NO: 6) | | |

PCR reactions are performed in 15 µl reaction volumes using the following PCR parameters:

| Component | Stock Concentration | Aliquot Volume | Final Concentration in PCR |
|---|---|---|---|
| Extracted DNA | 20 ng/µg | 2.5 µL | 2 ng/µg |
| AccuQuant ™ Custom SuperMix* | 2X | 7.5 µL | 1X |
| BVAB 2 F | 10 µM | 1.2 µL | 800 nm |
| BVAB 2 R2 | 10 µM | 1.2 µL | 800 nm |
| BVAB 2 Pr | 10 µM | 0.3 µL | 200 nm |
| Nuclease free H$_2$O | | 2.3 µL | |

*2x reaction buffer containing dNTP/dUTP, iTaq, MgCl$_2$, UNG, and stabilizers.

Four tubes are reserved for controls. The positive controls are to be diluted from the BVAB2 vector pBVAB2CLO and consist of the following:

| Control | Concentration | Final Copies in the Reaction |
|---|---|---|
| Positive High | 100,000,000 copies/µl | 10,000,000 |
| Positive Middle | 1,000,000 copies/µl | 100,000 |
| Positive Low | 10,000 copies/µl | 1,000 |
| NTC | N/A | 0 |

Dilution of the positive control from a $10^8$ copies/µl plasmid stock is performed. Programming a Real-Time PCR run and its profile conditions are carried out by the following steps:

| Step | Time | Temperature | Reason |
|---|---|---|---|
| Hold | 2 minutes | 50° C. | UNG activity |
| Hold | 5 minutes | 95° C. | Inactivate UNG Activate DNA polymerase Initial Denaturation |
| Cycling (40 cycles) | 10 seconds | 95° C. | Denaturation |
| | 45 seconds | 60° C. | Annealing & Extension Acquiring on FAM |

D. *Gardnerella vaginalis* by Real-Time PCR on Bio-Rad CFX

The present real-time PCR assay using Bio-Rad CFX provides a rapid, specific and sensitive detection of *Gardnerella vaginalis*. Biological sample, such as cervical swab, is obtained (e.g., via OneSwab). DNA is isolated using QIAamp DNA Mini Kit from Qiagen. The following primers were constructed commercially from IDT Technologies:

| Primer | Sequence 5' to 3' | Location | Product |
|---|---|---|---|
| GRO ES-7-F | GCAATCGCGTAGATGCGCTTGTTA (SEQ ID NO: 7) | Histidinol-phosphate | 95 bp |
| GRO ES-7-R | GAAGTTTGCATACGGCTCGGCAAT (SEQ ID NO: 8) | aminotransferase gene (HPAT) | |
| GRO ES-7-Pr-1 | /56-FAM/AGCGTAATCGCGTTG TAAGCGGTTTGC/3BHQ_1/ (SEQ ID NO: 9) | | |

PCR reactions are performed in 15 µl reaction volumes using the following PCR parameters:

| Component | Stock | Aliquot Volume | Final Concentration |
|---|---|---|---|
| Extracted DNA | 20 ng/µg | 2.5 µL | 2 ng/µg |
| Biorad qPCR Mastermix * | 2X | 7.5 µL | 1X |
| GRO ES-7-F | 10 µM | 1.2 µL | 800 nm |
| GRO ES-7-R | 10 µM | 1.2 µL | 800 nm |
| GRO ES-7-Pr-1 | 10 µM | 0.3 µL | 200 nm |
| H2O | | 2.3 µL | |

* 2x reaction buffer containing dNTP/dUTP, iTaq, MgCl$_2$, UNG, and stabilizers.

Four tubes are reserved for controls. The positive controls are to be diluted from the *Gardnerella vaginalis* vector pGVagL and consist of the following:

| Control | Concentration | Final Copies in the Reaction |
|---|---|---|
| Positive High | 100,000,000 copies/µl | 10,000,000 |
| Positive Middle | 1,000,000 copies/µl | 100,000 |
| Positive Low | 10,000 copies/µl | 1,000 |
| NTC | N/A | 0 |

Dilution of the positive control from a $10^8$ copies/µl plasmid stock is prepared. Programming a Real-Time PCR run and its profile conditions are carried out by the following steps:

| Step | Time | Temperature | Reason |
|---|---|---|---|
| Hold | 2 minutes | 50° C. | UNG activity |
| Hold | 5 minutes | 95° C. | Inactivate UNG Activate DNA polymerase Initial Denaturation |
| Cycling (40 cycles) | 10 seconds | 95° C. | Denaturation |
| | 45 seconds | 60° C. | Annealing & Extension Acquiring on FAM |

E. Real-Time PCR Assay for *Lactobacillus*

The present real-time PCR assay provides a rapid, specific and sensitive detection for *Lactobacillus iners*, *Lactobacillus crispatus*, *Lactobacillus gasseri*, and *Lactobacillus jensenii*. The present real-time PCR assay allows speciation and quantitation of the four major vaginal *Lactobacillus* species: *Lactobacillus iners*, *Lactobacillus crispatus*, *Lactobacillus gasseri*, and *Lactobacillus jensenii*. Biological sample, such as cervical swab, is obtained (e.g., via One-Swab). DNA is isolated using QIAamp DNA Mini Kit from Qiagen. The following primers were constructed commercially from IDT Technologies:

| Primer | Sequence 5' to 3' | Location | Product |
|---|---|---|---|
| Lactob_tuf-S14 | CGTGGTTCAGCWTTGAAGGC (SEQ ID NO: 13) | *Lactobacillus* tuf gene | 136 bp |
| Lactob_tuf-AS20 | CTTCAACTGGCATYAAGAATGGC (SEQ ID NO: 14) | Elongation factor Tu | |
| Lac.iners-TM | /5HEX/ AGGCGATCCAGAACAAGAAGCAG /3BHQ_1/ (SEQ ID NO: 15) | | |
| Lac.crispatus-TM | /56-ROXN/ AGGCGACAAGGAAGCTCAAGAAC /3BHQ_2/ (SEQ ID NO: 16) | | |
| Lac.gasseri-TM | /56-FAM/ AGGTGACCCAGAACAACAAGACG /3BHQ_1/ (SEQ ID NO: 17) | | |
| Lac.jensenii-TM | /5Cy5/ AGGTGACCCAGAACAAGAAAAGGT /3BHQ_2/ (SEQ ID NO: 18) | | |

PCR reactions are performed in 15 µl reaction volumes using the following PCR parameters:

| Component | Stock | Aliquot Volume | Final Concentration |
|---|---|---|---|
| Extracted DNA | 20 ng/µg | 2.5 µl | 2 ng/µg |
| Quanta qPCR Mastermix * | 2X | 7.5 µl | 1X |
| Lactob_tuf-S14 Primer | 10 µM | 1.2 µl | 800 nm |
| Lactob_tuf-AS20 Primer | 10 µM | 1.2 µl | 800 nm |
| *Lac. iners*-TM Probe | 10 µM | 0.15 µl | 100 nm |
| *Lac. crispatus*-TM Probe | 10 µM | 0.15 µl | 100 nm |
| *Lac. gasseri*-TM Probe | 10 µM | 0.15 µl | 100 nm |
| *Lac. jensenii*-TM Probe | 10 µM | 0.15 µl | 100 nm |
| H2O | — | 2 µl | — |

* 2x reaction buffer containing dNTP/dUTP, iTaq, MgCl$_2$, UNG, and stabilizers.

Four tubes are reserved for controls. The positive controls are to be diluted from four vector plasmids: pL.inersSB, pL.crispatusSB, pL.gasseriSB, pLjenseniiSB and consist of the following:

| Control | Concentration | Final Copies in the Reaction |
|---|---|---|
| Positive High | 100,000,000 copies/µl | 10,000,000 |
| Positive Middle | 1,000,000 copies/µl | 100,000 |
| Positive Low | 10,000 copies/µl | 1,000 |
| NTC | N/A | 0 |

Dilution of the positive control from a $10^8$ copies/µl plasmid stock is prepared. Programming a Real-Time PCR run and its profile conditions are carried out by the following steps:

| Step | Time | Temperature | Reason |
|---|---|---|---|
| Hold | 2 minutes | 50° C. | UNG activity |
| Hold | 5 minutes | 95° C. | Inactivate UNG, Activate DNA polymerase, Initial Denaturation |
| Cycling (40 cycles) | 10 seconds | 95° C. | Denaturation |
| | 45 seconds | 60° C. | Annealing & Extension Acquiring on FAM, HEX, ROX and Cy5 |

All publications and patents cited in this specification are herein incorporated by reference in their entirety. Various modifications and variations of the described composition, method, and systems of the invention will be apparent to those skilled in the art without departing from the scope and spirit of the invention. Although the invention has been described in connection with specific preferred embodiments and certain working examples, it should be understood that the invention as claimed should not be unduly limited to such specific embodiments. Various modifications for carrying out the invention that are obvious to those skilled in the field of molecular biology, recombinant expression and related fields are intended to be within the scope of the following claims.

TABLE 6

Specificity of *Lactobacillus* qPCR Fluorescent DNA Probes Against 21 *Lactobacillus* Species

| Lactobacillus species | ATCC # | L. crispatus probe | L. gasseri Probe | L. jensenii probe | L. iners probe |
|---|---|---|---|---|---|
| Lactobacillus acidophilus | 314 | − | − | − | − |
| Lactobacillus animalis | 35046 | − | − | − | − |
| Lactobacillus brevis | 14869 | − | − | − | − |
| Lactobacillus buchneri | 4005 | − | − | − | − |
| Lactobacillus casei | 393 | − | − | − | − |
| Lactobacillus crispatus | 33197 | + | − | − | − |
| Lactobacillus delbrueckii | 7830 | − | − | − | − |
| Lactobacillus fermentum | 9338 | − | − | − | − |
| Lactobacillus gasseri | 19992 | − | + | − | − |
| Lactobacillus hilgardii | 8290 | − | − | − | − |
| Lactobacillus iners | 55195 | − | − | − | + |
| Lactobacillus jensenii | 25258 | − | − | + | − |
| Lactobacillus johnsonii | 33200 | − | + | − | − |
| Lactobacillus plantarum | 8014 | − | − | − | − |
| Lactobacillus reuteri | 23272 | − | − | − | − |
| Lactobacillus rhamnosus | 7469 | − | − | − | − |
| Lactobacillus ruminis | 27780 | − | − | − | − |
| Lactobacillus sakei | 15521 | − | − | − | − |
| Lactobacillus salivarius | 11741 | − | − | − | − |
| Lactobacillus sharpeae | 49974 | − | − | − | − |
| Lactobacillus vaginalis | 49540 | − | − | − | − |

TABLE 7

Specificity of *G. vaginalis*, *A. vaginae*, BVAB2 and *Megasphaera* qPCRs Against 31 Bacterial Species and Human DNA

| Microbial species | ATCC strain # | G. vaginalis qPCR | A. vaginae qPCR | BVAB2 qPCR | Megasphaera qPCR |
|---|---|---|---|---|---|
| Atopobium vaginae | BAA-55 | − | + | − | − |
| Bacteroides ureolyticus | 33387 | − | − | − | − |
| Candida albicans | 90028 | − | − | − | − |
| Corynebacterium genitalium | 33030 | − | − | − | − |
| Cryptococcus neoformans | 32045 | − | − | − | − |
| Enterobacter aerogenes | 13048 | − | − | − | − |
| Enterococcus faecalis | 700221 | − | − | − | − |
| Enterococcus faecium | 19434 | − | − | − | − |
| Escherichia coli | 11303 | − | − | − | − |
| Gardnerella vaginalis | 49145 | + | − | − | − |
| Klebsiella oxytoca | 13182 | − | − | − | − |
| Leptotrichia buccalis | 14201 | − | − | − | − |
| Listeria monocytogenes | 7644 | − | − | − | − |
| Mobiluncus curtisii | 35242 | − | − | − | − |
| Moraxella catarrhalis | 25238 | − | − | − | − |
| Mycoplasma hominis | 15488 | − | − | − | − |
| Neisseria gonorrhoeae | 49226 | − | − | − | − |
| Peptococcus niger | 27731 | − | − | − | − |
| Peptostreptococcus anaerobius | 27337 | − | − | − | − |
| Prevotella bivia | 29303 | − | − | − | − |
| Proteus mirabilis | 29906 | − | − | − | − |
| Pseudomonas aeruginosa | BAA427 | − | − | − | − |
| Salmonella typhimurium | 49416 | − | − | − | − |
| Staphylococcus aureus | 25923 | − | − | − | − |
| Staphylococcus epidermidis | 12228 | − | − | − | − |
| Streptococcus agalactiae | A909 | − | − | − | − |
| Streptococcus pyogenes | 51339 | − | − | − | − |
| Ureaplasma urealyticum | 27618 | − | − | − | − |
| Human DNA female | (Promega G1521) | − | − | − | − |

TABLE 10

Coexistence of Bacterial Species in Vaginal Swabs as Determined by qPCR

|  | L. crispatus | L. jensenii | L. gasseri | L. iners | G. vaginalis | A. vaginae | BVAB2 | Megasphaera Type 1 | Megasphaera Type 2 |
|---|---|---|---|---|---|---|---|---|---|
| L. crispatus (51) | — | 14 (27%) | 2 (4%) | 22 (43%) | 8 (16%) | 1 (2%) | 0 (0%) | 0 (0%) | 0 (0%) |
| L. jensenii (30) | 14 (47%) | — | 2 (7%) | 20 (67%) | 8 (27%) | 8 (27%) | 0 (0%) | 0 (0%) | 0 (0%) |
| L. gasseri (20) | 2 (10%) | 2 (10%) | — | 3 (15%) | 8 (45%) | 8 (45%) | 0 (0%) | 0 (0%) | 0 (0%) |
| L. iners (108) | 22 (20%) | 20 (19%) | 3 (3%) | — | 54 (50%) | 49 (45%) | 31 (29%) | 36 (33%) | 10 (9%) |
| G. vaginalis (76) | 8 (11%) | 8 (11%) | 8 (11%) | 54 (71%) | — | 57 (75%) | 37 (49%) | 41 (54%) | 11 (14%) |
| A. vaginae (62) | 1 (2%) | 2 (3%) | 1 (2%) | 49 (79%) | 57 (92%) | — | 40 (65%) | 41 (66%) | 11 (18%) |
| BVAB2 (40) | 0 (0%) | 0 (0%) | 0 (0%) | 31 (78%) | 37 (93%) | 40 (100%) | — | 32 (80%) | 11 (28%) |
| Megasphaera Type 1 (44) | 0 (0%) | 0 (0%) | 0 (0%) | 36 (82%) | 41 (93%) | 41 (93%) | 32 (73%) | — | 6 (14%) |
| Megasphaera Type 2 (11) | 0 (0%) | 0 (0%) | 0 (0%) | 10 (91%) | 11 (100%) | 11 (100%) | 11 (100%) | 6 (55%) | — |

Correlation coefficient (r):  +     -1 < r < -0.2 (negative association)

-0.2 < r < 0.2 (none or weak association)

*     0.2 < r < 1 (positive association)

What is claimed is:

1. A kit comprising:

(a) a first forward primer, a first reverse primer and a first fluorescently-labeled probe against *Gardnerella vaginalis*, said first forward primer consisting of SEQ ID NO: 7, said first reverse primer consisting of SEQ ID NO: 8, and said first probe consisting of SEQ ID NO: 9;

(b) a second forward primer, a second reverse primer, and a second fluorescently-labeled probe against *Lactobacillus iners*, said second forward primer consisting of SEQ ID NO: 13, said second reverse primer consisting of SEQ ID NO: 14, and said second probe consisting of SEQ ID NO: 15; and (c) an instruction for profiling vaginal microflora in a woman comprising instructions for calculating the relative amount of *Lactobacillus iners* and *Gardnerella vaginalis* in a biological sample obtained from the woman.

2. The kit of claim 1, further comprising:

(d) a third forward primer, a third reverse primer and a third fluorescently-labeled probe against *Atopobium vaginae*, said third forward primer consisting of SEQ ID NO: 1, said third reverse primer consisting of SEQ ID NO: 2, and said third probe consisting of SEQ ID NO: 3;

(e) a fourth forward primer, a fourth reverse primer and a fourth fluorescently-labeled probe against BVAB2, said fourth forward primer consisting of SEQ ID NO: 4, said fourth reverse primer consisting of SEQ ID NO: 5, and said fourth probe consisting of SEQ ID NO: 6;

(f) a fifth, sixth and seventh fluorescently-labeled probes against *Lactobacillus crispatus, Lactobacillus gasseri* and *Lactobacillus jensenii* respectively, said fifth probe consisting of SEQ ID NO: 16, said sixth probe consisting of SEQ ID NO: 17 and said seventh probe consisting of SEQ ID NO: 18; and (g) a fifth forward primer, a fifth reverse primer against *Megasphaera*, and an eighth and ninth fluorescently-labeled probe against *Megasphaera* Type 1 and *Megasphaera* Type 2, respectively, said fifth forward primer consisting of SEQ ID NO: 19, said fifth reverse primer consisting of SEQ ID NO: 20, and said eighth probe consisting of SEQ ID NO: 21 and said ninth probe consisting of SEQ ID NO: 22.

3. A method of diagnosing transitional vaginal microflora status in a woman, comprising the steps of:

(a) quantifying the amount of individual microflora for *Lactobacillus* crispatus, *Lactobacillus gasseria*, *Lactobacillus jensenni*, *Lactobacillus iners*, *Gardnerella vaginalis*, *Atopobium vaginae*, *Megasphaera* Type 1, *Megasphaera* Type 2 and BVAB2 in a biological sample obtained from a woman, wherein said quantifying step is performed by using a molecular assay selected from the group consisting of qPCR and multiplex qPCR;

(b) calculating the sum of said amount of individual microflora in said biological sample to obtain a total amount of microflora;

(c) calculating the sum of said amount of *Lactobacillus iners* and *Gardnerella vaginalis* in said biological sample;

(d) calculating the relative amount of said *Lactobacillus iners* and *Gardnerella vaginalis* in said biological sample by dividing said sum amount of *Lactobacillus iners* and *Gardnerella vaginalis* by said total amount of microflora, wherein, said relative amount of *Lactobacillus iners* and *Gardnerella vaginalis*, when exceeding 50% of said total amount of microflora, is indicative of a transitional vaginal microflora; and (e) diagnosing said woman with transitional vaginal microflora status based on said relative amount of *Lactobacillus iners* and *Gardnerella vaginalis* in said biological sample;

wherein:

the quantifying of *Lactobacillus crispatus* is performed using a multiplex qPCR and SEQ ID NO: 13, SEQ ID NO: 14 and SEQ ID NO: 16;

the quantifying of *Lactobacillus gasseria* is performed using a multiplex qPCR and SEQ ID NO: 13, SEQ ID NO: 14 and SEQ ID NO: 17;

the quantifying of *Lactobacillus jensenni* is performed using a multiplex qPCR and SEQ ID NO: 13, SEQ ID NO: 14 and SEQ ID NO: 18;

the quantifying of *Lactobacillus iners* is performed using a multiplex qPCR and SEQ ID NO: 13, SEQ ID NO: 14 and SEQ ID NO: 15;

the quantifying of *Atopobium vaginae* is performed using SEQ ID NO: 1, SEQ ID NO: 2 and SEQ ID NO: 3;

the quantifying of BVAB2 is performed using SEQ ID NO: 4, SEQ ID NO: 5 and SEQ ID NO: 6;

the quantifying of *Gardnerella vaginalis* is performed using SEQ ID NO: 7, SEQ ID NO: 8 and SEQ ID NO: 9;

the quantifying of *Megasphaera* Type 1 is performed using a multiplex qPCR and SEQ ID NO: 19, SEQ ID NO: 20 and SEQ ID NO: 21; and the quantifying of *Megasphaera* Type 2 is performed using a multiplex qPCR and SEQ ID NO: 19, SEQ ID NO: 20 and SEQ ID NO: 22.

* * * * *

SEQUENCE LISTING

<160> NUMBER OF SEQ ID NOS: 22

<210> SEQ ID NO 1
<211> LENGTH: 23
<212> TYPE: DNA
<213> ORGANISM: Homo sapiens

<400> SEQUENCE: 1
agaccttcct ccatagcaat ggg                                       23

<210> SEQ ID NO 2
<211> LENGTH: 23
<212> TYPE: DNA
<213> ORGANISM: Homo sapiens

<400> SEQUENCE: 2
cctcagttct acttccgcac cac                                       23

<210> SEQ ID NO 3
<211> LENGTH: 21
<212> TYPE: DNA
<213> ORGANISM: Homo sapiens

<400> SEQUENCE: 3
acgtggtcgc caggcatagc c                                         21

<210> SEQ ID NO 4
<211> LENGTH: 24
<212> TYPE: DNA
<213> ORGANISM: Homo sapiens

<400> SEQUENCE: 4
aaaactcttt ggacagggac gaag                                     24

<210> SEQ ID NO 5
<211> LENGTH: 25

<212> TYPE: DNA
<213> ORGANISM: Homo sapiens

<400> SEQUENCE: 5
ccagcactca agctaaacag tttgt                                              25

<210> SEQ ID NO 6
<211> LENGTH: 25
<212> TYPE: DNA
<213> ORGANISM: Homo sapiens

<400> SEQUENCE: 6
cacttatcta gccgcctaca cgccc                                              25

<210> SEQ ID NO 7
<211> LENGTH: 24
<212> TYPE: DNA
<213> ORGANISM: Homo sapiens

<400> SEQUENCE: 7
gcaatcgcgt agatgcgctt gtta                                               24

<210> SEQ ID NO 8
<211> LENGTH: 24
<212> TYPE: DNA
<213> ORGANISM: Homo sapiens

<400> SEQUENCE: 8
gaagtttgca tacggctcgg caat                                               24

<210> SEQ ID NO 9
<211> LENGTH: 25
<212> TYPE: DNA
<213> ORGANISM: Homo sapiens

<400> SEQUENCE: 9
agcgtaatcg cgttgtaagc ggttt                                              25

<210> SEQ ID NO 10
<211> LENGTH: 20
<212> TYPE: DNA
<213> ORGANISM: Homo sapiens

<400> SEQUENCE: 10
gagcaccagg tggtctcctc                                                    20

<210> SEQ ID NO 11
<211> LENGTH: 23
<212> TYPE: DNA
<213> ORGANISM: Homo sapiens

<400> SEQUENCE: 11
cagccacata ccaggaaatg agc                                                23

<210> SEQ ID NO 12
<211> LENGTH: 24
<212> TYPE: DNA
<213> ORGANISM: Homo sapiens

<400> SEQUENCE: 12
ctggcattgc cctcaacgac cact                                               24

<210> SEQ ID NO 13

```
<211> LENGTH: 20
<212> TYPE: DNA
<213> ORGANISM: Homo sapiens

<400> SEQUENCE: 13
cgtggttcag cwttgaaggc                                                      20

<210> SEQ ID NO 14
<211> LENGTH: 23
<212> TYPE: DNA
<213> ORGANISM: Homo sapiens

<400> SEQUENCE: 14
cttcaactgg catyaagaat ggc                                                  23

<210> SEQ ID NO 15
<211> LENGTH: 23
<212> TYPE: DNA
<213> ORGANISM: Homo sapiens

<400> SEQUENCE: 15
aggcgatcca gaacaagaag cag                                                  23

<210> SEQ ID NO 16
<211> LENGTH: 23
<212> TYPE: DNA
<213> ORGANISM: Homo sapiens

<400> SEQUENCE: 16
aggcgacaag gaagctcaag aac                                                  23

<210> SEQ ID NO 17
<211> LENGTH: 23
<212> TYPE: DNA
<213> ORGANISM: Homo sapiens

<400> SEQUENCE: 17
aggtgaccca gaacaacaag acg                                                  23

<210> SEQ ID NO 18
<211> LENGTH: 24
<212> TYPE: DNA
<213> ORGANISM: Homo sapiens

<400> SEQUENCE: 18
aggtgaccca gaacaagaaa aggt                                                 24

<210> SEQ ID NO 19
<211> LENGTH: 23
<212> TYPE: DNA
<213> ORGANISM: Homo sapiens

<400> SEQUENCE: 19
cttccgcaat ggacgaaagt ctg                                                  23

<210> SEQ ID NO 20
<211> LENGTH: 22
<212> TYPE: DNA
<213> ORGANISM: Homo sapiens

<400> SEQUENCE: 20
cacgtagtta gccgtggctt tc                                                   22
```

```
<210> SEQ ID NO 21
<211> LENGTH: 23
<212> TYPE: DNA
<213> ORGANISM: Homo sapiens

<400> SEQUENCE: 21
cggacggata ctgttggcat ccg                                          23

<210> SEQ ID NO 22
<211> LENGTH: 24
<212> TYPE: DNA
<213> ORGANISM: Homo sapiens

<400> SEQUENCE: 22
tgatggctat ttaccacctt gccg                                         24
```